(12) United States Patent
Jervis et al.

(10) Patent No.: US 7,919,319 B2
(45) Date of Patent: Apr. 5, 2011

(54) CULTURED CELL AND METHOD AND APPARATUS FOR CELL CULTURE

(75) Inventors: Eric Jervis, Waterloo (CA); John Ramunas, Ottawa (CA)

(73) Assignee: University of Waterloo, Waterloo, Ontario (CA)

( * ) Notice: Subject to any disclaimer, the term of this patent is extended or adjusted under 35 U.S.C. 154(b) by 875 days.

(21) Appl. No.: 10/582,975

(22) PCT Filed: Dec. 17, 2004

(86) PCT No.: PCT/CA2004/002138
§ 371 (c)(1),
(2), (4) Date: Jun. 15, 2006

(87) PCT Pub. No.: WO2005/059088
PCT Pub. Date: Jun. 30, 2005

(65) Prior Publication Data
US 2007/0161106 A1    Jul. 12, 2007

Related U.S. Application Data

(60) Provisional application No. 60/530,614, filed on Dec. 19, 2003.

(51) Int. Cl.
*C12N 5/02* (2006.01)
(52) U.S. Cl. .................. 435/395; 435/292.1; 435/305.4
(58) Field of Classification Search .................. None
See application file for complete search history.

(56) References Cited

U.S. PATENT DOCUMENTS

| | | | |
|---|---|---|---|
| 5,976,826 A | 11/1999 | Singhvi et al. | |
| 6,653,124 B1 | 11/2003 | Freeman | |
| 6,855,542 B2 * | 2/2005 | DiMilla et al. | 435/289.1 |
| 6,866,824 B2 * | 3/2005 | Lafferty et al. | 422/82.05 |
| 2003/0129671 A1 | 7/2003 | Wilding et al. | |
| 2004/0241203 A1* | 12/2004 | Shakesheff et al. | 424/426 |

FOREIGN PATENT DOCUMENTS

| | | |
|---|---|---|
| EP | 1174497 A | 1/2002 |
| WO | 98/43123 A | 10/1998 |
| WO | 03/060061 A1 | 7/2003 |
| WO | 03/093406 A2 | 11/2003 |

OTHER PUBLICATIONS

Li, S. et al., "Effects of morphological patterning on endothelial cell migration", Biorheology 38 (2001), pp. 101-108.

Mata, A. et al., "Analysis of connective tissue progenitor cell behaviour on polydimethylsiloxane smooth and channel micro-textures", Biomedical Microdevices, 4:4 (2002), pp. 267-275.

Dertinger S.K.W. et al., "Gradients of substrate-bound Laminin orient axonal specification of neurons", Proc Natl Acad Sci USA Oct. 1, 2002, vol. 99, No. 20, pp. 12542-12547.

Taylor, A.M. et al., "Microfluidic Multicompartment Device for Neuroscience Research", Langmuir 2003, 19, pp. 1551-1556.

Yu, Q. et al., "Responsive biomimetic hydrogel valve for microfluidics", Applied Physics Letters, vol. 78, No. 17, Apr. 23, 2001, pp. 2589-2591.

Eggiins, B.R., "Chapter 5—Electrochemical Sensors and Biosensors", pp. 125-169, "Chemical Sensors and Biosensors", Analytical techniques in the Sciences, 2002, John Wiley & Sons. New York, 273 pp.

Whitesides, G.M., "The 'right' size in nanobiotechnology", Nature Biotechnology, vol. 21, No. 10, Oct. 2003, pp. 1161-1165.

Takayama S. et al., "Patterning cells and their environments using multiple laminar fluid flows in capillary networks", Proc. Natl. Acad. Sci. USA, vol. 96,May 1999, pp. 5545-5548.

Inoue, H. et al., "Long-term time-lapse cinemicrography of human erythroblasts under compression and without compression—direct measurement of generation time of each maturation stage", International Journal of Hematology, 58 (1993), pp. 1-8.

\* cited by examiner

*Primary Examiner* — James S Ketter

(57) ABSTRACT

One or more cells can be cultured when confined in space by barriers. The distance between barriers can be comparable to the size of a cell to be cultured. The space between barriers can also be sufficiently small to allow control of cell properties or monitoring of the cell(s) cultured therein. The cell(s) may be confined completely or may be mobile between two opposing barrier surfaces. The gap between two opposing barriers may be sufficiently narrow to allow only a monolayer of cells to be cultured. A barrier can be transparent. The surfaces of the barriers may have one or more pre-selected characteristics that mimic the characteristics of a biological niche of the cells(s). The number of cells in a cell culture may be limited to permit control of properties of individual cells. The cultured cell(s) may be monitored, such as imaged, over a long period of time, using standard bright field or fluorescent imaging techniques.

100 Claims, 12 Drawing Sheets

CULTURED CELL AND METHOD AND APPARATUS FOR CELL CULTURE

CROSS-REFERENCE TO RELATED APPLICATION

This application claims priority from U.S. provisional application No. 60/530,614, entitled "APPARATUS AND METHOD FOR CELL CULTURE" and filed Dec. 19, 2003, which is incorporated herein by reference.

FIELD OF THE INVENTION

The present invention relates generally to cell culture, and more particularly to cultured cells and apparatus and methods for cell culture.

BACKGROUND

Typically, cells are cultured in vitro by growing cells in a fluid or gel-like growth media in a sterile container under certain controlled conditions, including the temperature and pH. In many stem cell cultures, for example, cells are grown as free-floating aggregates in suspension in a media. However, in such cultures, the immediate vicinity of a cell, its microenvironment, is constantly changing such that a cell is exposed to a variable and uncontrolled local environment, which may not closely resemble the cell's in vivo environment. This results in a heterogenous mixture of cell types, even in cultures started with a single cell. The In vivo, molecules secreted by cells are important for their function and the function of neighbouring cells. However, in known culture systems, these molecules quickly diffuse away and are diluted such that the interactions of cells with locally-secreted molecules that occur in vivo is lost or is ineffective and one or more of the cells' normal functions thus may be affected. Additionally, in some traditional cell cultures cells tend to attach or adhere to the surface of the cell culture container, which may not be desirable for some cell types. For example, attachment of many stem or progenitor cells may not be desirable as it may promote differentiation and otherwise change the cell phenotype.

In known in vitro or ex vivo cell culture methods and apparatus it is difficult or impossible to control the properties and phenotype of individual cells, to trace cell division and lineage, and to monitor and record activity (behaviour) histories for each individual cell within the culture. Some conventional techniques for obtaining high resolution images of cultured cells, such as laser scanning confocal microscopy, are not suitable for long-term imaging of cultured cells. For example, in conventional high resolution imaging techniques such as laser scanning confocal microscopy, the cultured cells are usually exposed to high intensity light. As a result, light- or laser-induced phototoxicity can limit the time during which a live cell can be imaged. Further, it is generally expensive to obtain high resolution images of cells cultured using conventional techniques.

Therefore there is a need for increased control of a cell culture.

SUMMARY OF THE INVENTION

One or more cells can be cultured when confined in space by barriers. The cell(s) may be confined completely or may move laterally between two opposing barrier surfaces. The gap between two opposing barriers may be sufficiently narrow to allow only a monolayer of cells to be cultured. A barrier can be transparent.

As can be understood, culturing cells within a confined space can be advantageous. For example, it is possible to precisely control the environment of each cell and thus to provide a culturing environment that mirrors a biological niche. It is also possible to remove any particular cell from, or to add a cell to, an assembly of cultured cells. Further, confining cells between barriers can facilitate direct observation of cell growth and subcellular detail in live cells with imaging techniques such as standard bright field imaging or fluorescent imaging without the use of a confocal microscope or a laser imaging device. When cells are confined within the proximity of the in-focus-plane of an object lens, the image quality can significantly improve as compared to images of cells that can move away from the in-focus-plane.

Thus, in accordance with an aspect of the invention there is provided a method of cell culture. In this method, a cell is confined between first and second barriers. The barriers are spaced at a distance comparable to the size of the cell to contact the cell and prevent the cell from travelling toward or away from each of the first and second barriers. A culture substance is provided to the cell.

In accordance with another aspect of the invention there is provided a method for controlling properties of individual cells in a cell culture. In this method, a cell is confined in a space defined by at least two surfaces that contact the cell. The space has a size comparable to the size of the cell. Each of the surfaces the cell contacts has one or more pre-selected characteristics. The number of cells surrounding the cell is limited to permit control of properties of the cell. A culture substance is provided to the space. The pre-selected characteristics may be selected to mimic the characteristics of the biological niche of the cell.

In any of the above mentioned methods, a plurality of cells may be cultured between the barriers or surfaces. The plurality of cells may form a monolayer. The cultured cell(s) may be monitored, for example by using optical devices or sensors. The result of monitoring may be recorded. Further, an additional cell may be manually positioned adjacent a cultured cell so that the two cells can interact with each other.

In accordance with a further aspect of the invention, there is provided a method of forming an artificial tissue, which includes laying a monolayer of cells on another monolayer of cells and permitting cells in one monolayer to interact with cells of the other monolayer. Each monolayer of cells is cultured according to a method of the invention.

In accordance with a further aspect of the invention, there is provided a cell or an assembly of cells comprising a cell cultured in accordance with a method of the invention. The cell or assembly of cells may be used as an artificial tissue, organ, cell transplant, or in vitro fertilization.

In accordance with a further aspect of the invention there is provided a combination of a cell culture device and a cell culture. The combination includes a container defining a chamber for receiving a fluid culture medium and at least two barriers defining a space in the chamber. A cell is constrained in the space and in continuous contact with each one of the barriers during culturing. Each of the barriers has one or more pre-selected characteristics. The combination has means for providing to the space a culture substance at a predetermined rate, which may comprise one or more fluid passageways allowing fluid communication to and from the chamber. Means for regulating a fluid flow to or from the chamber may be included. Means for monitoring the cell constrained in the space may also be included.

In accordance with a further aspect of the invention, there is provided a combination of a cell culturing device and a cell culture. The combination includes a container defining a chamber for receiving a fluid culture substance and at least two barriers defining a space in the chamber. Each one of the barriers has one or more pre-selected characteristics. An assembly of two or more cells is constrained in the space so as to keep the assembly therein and in continuous contact with each of the barriers during culturing. The combination also includes means for providing to the space a culture substance at a predetermined rate. The assembly may include one or more layers of cells. For example, the assembly may include a monolayer of cells.

In accordance with a further aspect of the invention, there is provided an apparatus for culturing cells in a controlled artificial niche. The apparatus includes a container defining a chamber for receiving a fluid culture medium and at least two barriers defining a space in the chamber for cell culture. The inner surface of each of the barriers has one or more pre-selected characteristics. The space is sufficiently small to permit control of the properties of one or more individual cells cultured in the space. The apparatus also includes means for providing a culture substance to the space.

In accordance with a further aspect of the invention, a plurality of devices, each being one of the apparatus and combination described above, may be assembled together to form an assembly for cell culturing. Each one of the plurality of devices can be generally plate-shaped and the devices can be stacked in parallel.

In accordance with a further aspect of the invention, there is provided a method of cell culturing, which includes culturing one or more cells while restricting movement of the cell(s) such that each one of the cell(s) is in continuous contact with two opposing barrier surfaces. However, the cell(s) is (are) mobile between the barrier surfaces. The cell(s) can be imaged during culturing using a non-confocal imaging device, such as a bright field imaging device or a fluorescent imaging device including a differential interference contrast (DIC) imaging device.

Other aspects, features and advantages of the invention will become apparent to those of ordinary skill in the art upon review of the following description of specific embodiments of the invention in conjunction with the accompanying figures.

BRIEF DESCRIPTION OF THE DRAWINGS

In the figures, which illustrate exemplary embodiments of the invention.

DETAILED DESCRIPTION OF PREFERRED EMBODIMENTS

Figure 1:
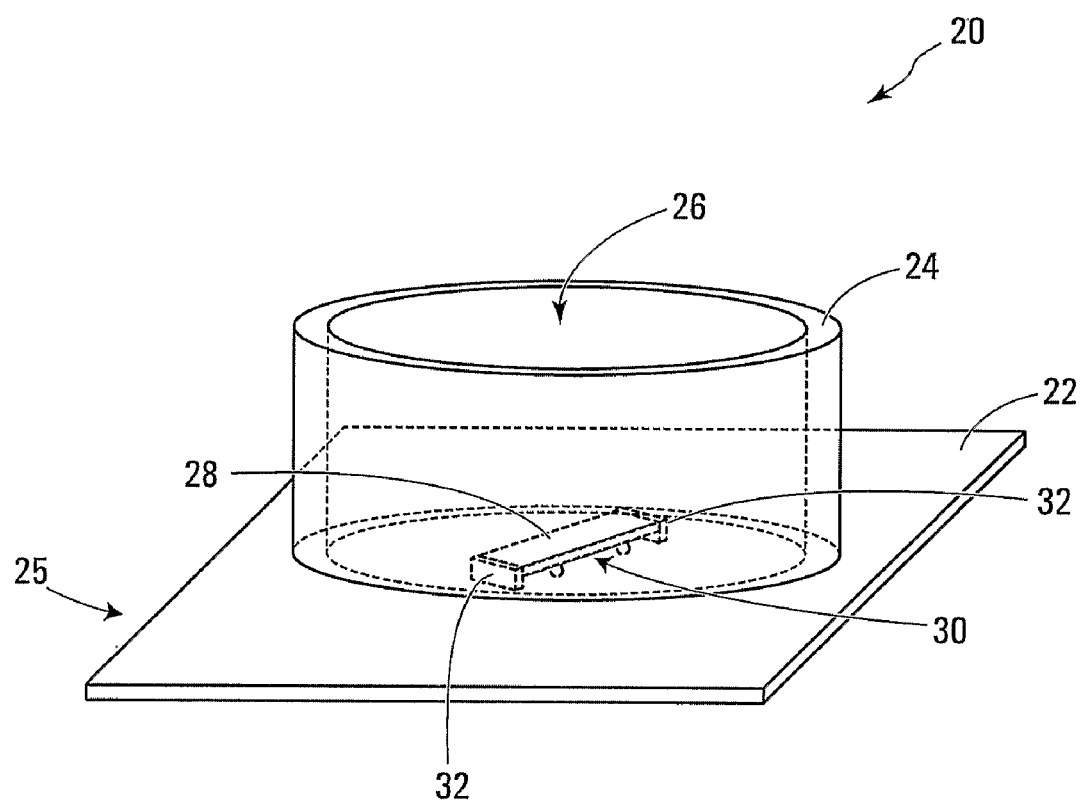
FIG. 1 is a perspective view of a cell culturing apparatus according to an embodiment of the invention.

The inventors have discovered that cell culture in vitro can be advantageously controlled by controlling the microenvironment of individual cells in a culture chamber. A cell's microenvironment is the local environment surrounding a cell or the immediate vicinity of a cell, also known as a niche. In this invention, the in vivo biological environment is referred to as the "natural niche" or interchangeably the "biological niche" and the in vitro micro-environment in cell culture is referred to as an "artificial niche".

The inventors have identified certain aspects of an artificial niche of a cell that can and may need to be controlled in order for the artificial niche to mimic the biological niche. One such aspect is the size and shape of the artificial niche as defined, at least in part, by neighbouring objects in contact with the cell; another aspect is the physical and/or chemical characteristics or properties of the surfaces that surround a cell to form an artificial niche; a further aspect is the supply of nutrients and removal of metabolites to and from the artificial niche. Further, monitoring and recording the characteristics of each individual cell and its microenvironment may facilitate the culturing of an individual cell with desirable properties such as a desired phenotype.

In an organism, a cell's microenvironment is highly specific to each cell type and to almost every cell; hence resulting in the complex patterning possible in, for example, the human body. The inventors have identified the requirements that a microenvironment of a cell needs to satisfy in order to control the characteristics of a cell, such as phenotype, and cell differentiation. When these requirements are satisfied in cell culture, more precise control can be obtained, in comparison with known systems. Potentially, a cultured cell can be controlled more precisely in an artificial niche than in a biological niche. To precisely control a cell's culture, its microenvironment needs to satisfy each of the following requirements in a way that is appropriate for a particular cell type: 1) the niche has appropriate size and shape; 2) the solid, liquid, gas, or other phases that form the boundaries and interior of a niche have appropriate chemical and physical properties; 3) the niche has appropriate sources and sinks of solutions. Preferably, the artificial niche and individual cell characteristics can be monitored. The inventors have created artificial niches that meet these requirements.

In a culture, artificial niches may exist alone or in contiguous groups. In other words, a culture device may contain more than one artificial niche. In contrast to a cell aggregate in bulk culture, where the microenvironment around each cell is random and uncontrolled, artificial niches formed in embodiments of the invention are defined and controlled. This can be achieved in a large group of cells by defining and controlling the boundary around each cell and the solutions diffusing into the group, so that the niche around every cell in the group is effectively defined and controlled. Monitoring enables unwanted cells to be eliminated (e.g. through photo-ablation), reproducing the function of an organism's immune system.

Separate niches or contiguous groups of niches may also be connected together by channels so that some cells in a culture device are not in physical contact with other cells but are in chemical communication. A culture device may contain any combination of separate niches, niche assemblies, and niches that are not in physical contact but are in chemical or other communication.

More specifically, the inventors have established that by confining or constraining a cell within a predefined space such as between two or more non-cellular barriers or neighbouring cells, where the space has a size comparable to the size of the cell or its biological niche, the characteristics of its artificial niche can be effectively controlled and/or monitored. When a cultured cell is confined in a predefined space, it is possible to control its artificial niche to closely model its biological niche. For instance, the confining barriers may define desired sizes and shapes of the space, may have desired surface characteristics and properties, and may be connected with appropriate sources and sinks. Further, when a cell is confined, individual cell's growth and division may be monitored, as the cell's movement is limited. As can be appreciated, to achieve the benefits mentioned above, the pre-defined space need only to have a size comparable to the size of the cell or its biological niche in one dimension, although in various embodiments, a target cell may be advantageously confined or constrained on all sides A cell can be confined between two barriers that are spaced apart at a distance comparable to the size of the cell such that the barriers contact the cell to prevent the cell from travelling towards or away from each of the barriers.

The barriers are thus formed by at least two separate surfaces that the cell contacts and is therefore distinguishable from a single continuous barrier that may be formed around a cell, for example, by seeding a cell in a continuous gel.

A barrier limits the movement of the cell relative to the barrier. It can be made of any sufficiently rigid, non-cellular material and can be of various forms. It can be permeable, selectively permeable, or impermeable. For example, a barrier can be a glass plate, a porous membrane, or a gel. As the barrier functions to create a microenvironment that facilitates the desired regulation, phenotype, behaviour, function or proliferation of a cell, the appropriate choice of a barrier will depend on the particular objective of the cell culture as would be apparent to a skilled person and as further described below.

The smallest distance between the barriers is comparable to the size of a confined cell so that, while the movement of the cell is limited, the cell is not overly compressed to the extent that the cell may be adversely or inadvertently affected, such as being damaged, killed, or caused to function unnaturally.

As will be further described below, in some embodiments of the invention, the microenvironment of a cell can be controlled, at least in part, by controlling the physical, chemical and biological characteristics or properties of the surfaces that a cell contacts. The microenvironment of the cell can also be controlled at least in part, by controlling the manner in which culturing substances are provided to and distributed in the cell niche. For example, for fluid culture media, fluid flow directions and rates, concentrations of certain components in the media, and concentration gradients can be controlled or regulated. The culturing substances may include a culturing fluid containing growth factors, nutrients, (dissolved) oxygen and the like. The fluid flow can be regulated, for example, to create concentration gradients. It will be understood that fluid flow can be controlled by regulating either diffusive flux or convection rate, or both. As can be appreciated, culture substances can be provided to a cell niche in various ways and through various structures. For example, a fluid can be provided through a fluid conduit, a permeable plate, or an opening in the culture chamber. Culture substances can also be provided to a cell by other cells.

As will be understood, by controlling the artificial niches in manners described herein, biological niches can be sufficiently replicated and cultured cells with desirable properties can be obtained.

As will be further described below, in some embodiments of the invention, cell growth and division can be monitored (e.g. optically) and recorded, on an individual cell basis. The lineage history of each cultured cell can be monitored and recorded. Thus, specific information on the properties of each individual cell can be obtained. Precise knowledge of cell property and history is useful both in controlling the culturing of cells and in later applications of cultured cells.

Specific exemplary embodiments of the invention, including methods and apparatus, are described below with reference to the accompanying drawings.

Referring to FIG. 1, an exemplary embodiment of the invention includes a cell culturing apparatus 20. Apparatus 20 has a base plate 22 and a tube 24 mounted on base plate 22, thus forming a container 25 which defines a chamber 26 for receiving and containing a liquid culture medium. Apparatus 20 may further include a cover (not shown) removably mounted by a hinge on tube 24 to avoid contaminants from entering the chamber formed by the container. In different embodiments the cover may be loosely fitting transparent glass or transparent membrane that allows for gas exchange.

A cover plate 28 is positioned above and opposite base plate 22 inside chamber 26. Base plate 22 and cover plate 28 are spaced apart at a desired distance as will be further described below, and thus define a niche chamber 30 therebetween, within which cells may be constrained or confined. As will be described further below, base plate 22 and cover plate 28 form barriers that constrain one or more cells therebetween so that the cells cannot travel toward or away from the plates and are kept in continuous contact with the plates. The barrier surfaces can be generally planar or curved.

Figure 2:
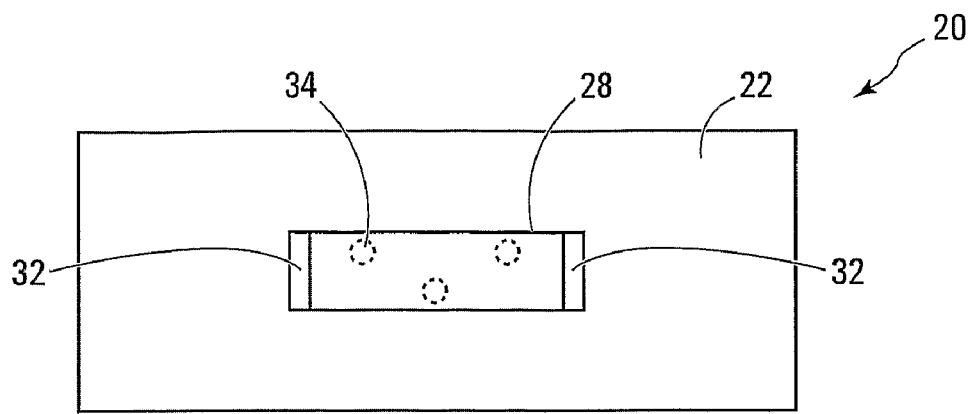
FIG. 2 is a partial top plan view of the apparatus of FIG. 1.
Figure 3:
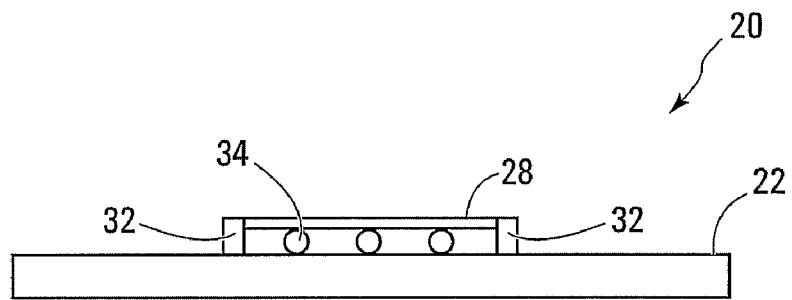
FIG. 3 is a front plan view of the portion shown in FIG. 2.

Referring to FIGS. 2 to 3, base plate 22 and cover plate 28 may be held in position at two opposite ends of plate 28 by an adhesive material, such as a pair of silicone glue gussets 32. Alternatively, the plates may be held together by other chemical or mechanical holding mechanisms. Cover plate 28 may be removably mounted by a hinge on base plate 22. For example, one end of cover plate 28 may be hinged to base plate 22 and the opposite end may be clipped to base plate 22. Niche chamber 30 may be further defined by side plates (not shown) joining the base plate 22 and cover plate 28 to form a closed chamber and in this embodiment, may have one or more openings to allow fluid communication between niche chamber 30 and chamber 26 through the opening(s) (it being understood that when side plates are not present, base plate 22 and cover plate 28 define an open niche chamber 30 in fluid communication with chamber 26).

As can be appreciated, plates 22 and 28 should be close enough to constrain a cell therebetween by slightly compressing the cell without causing undesirable results or inadvertent effects such as irreversible damage of the cell, or unintended cell differentiation, cell reaction, or change of cell functions.

The materials suitable for constructing containers defining a culture chamber are well known to a person skilled in the art. For example, tube 24 may be made of glass or plastic such as polystyrene. Transparent materials may be advantageous, such as to permit cells to be optically monitored. Tube 24 may have any desirable size or shape and may be large enough to accommodate multiple niche chambers.

Plates 22 and 28 may have various sizes, shapes, and thicknesses. The thickness of base plate 22 can be selected to accommodate cell monitoring requirements, such as being thinner than the maximum working distance of an imaging device. Plate 22 may be of a thickness of a typical microscope cover slip. Plates 22 and 28 should be thick enough to be sufficiently rigid. In different embodiments, however, one or both of plates 22 and 28 may be somewhat flexible, as will be more fully described below.

Plates 22 and 28 may be made of the same or different materials. Suitable materials include (porous) glass, contact lens material, glass polystyrene matrix or polyethylene, natural or synthetic biocompatible polymers, or other biocompatible materials selected according to the cells to be cultured, as will be further described below. For example, plates 22 and 28 may be made of untreated, bio-inert glass or untreated polystyrene.

One or more of plates 22 and 28 may also be derivatized or coated before or during culture with extracellular matrix molecules, adhesion ligands, growth factors, receptors, and the like. The use and benefits of coating the inner surfaces of a culture chamber is known to a person skilled in the art.

As can be appreciated, cells can attach to the surfaces they contact, which may or may not be desirable. To limit attachment of cells, the inner surfaces of the plates may be made of or lined with substances that limit adhesion, such as untreated polystyrene, glass, polyacrylamide gel, or anti-adhesive biomolecules including polysaccharides, proteoglycans, proteins, or polyethylene oxide. Thus, the cells can be confined without necessarily attaching or adhering to plates 22 and 28. For example, one or both of the plates 22 and 28 may be coated with materials that affect cell attachment and behaviour, such as poly(dimethylacrylamide) or dimethyldichlorosilane.

The inner surfaces with certain affinity to a certain type of cells can also be used to control the cell growth. When the surfaces have no or little affinity to the cultured cells, the cultured cells may be confined but do not attach to the surfaces of the cover plates, and thus they are mobile and can move laterally along the inner surfaces of the plates. For example, cells may move due to concentration ingredient in the culture medium or they may be forced to move by an external force such as a magnetic force. Cells may orient in a certain way depending on the surface properties. The surface materials may also be so selected as to test compounds that attract or repel a certain cell.

The inner surfaces of plates 22 and 28 (meaning the surfaces that contact the cell) may be made of a material specifically selected to either facilitate or inhibit the growth of a certain cell.

Each of plates 22 and 28 (and any side plates if present) may be permeable (or non-permeable) to a gas. A gas permeable plate may be necessary when it is desirable to perfuse a gas into niche chamber 30. Cover plate 28 may also be permeable to a given component of a liquid culture medium, so that the component may be transported into niche chamber 30 through plate 28, instead of, or in addition to, openings of niche chamber 30. Plates 22 and 28 may be transparent or opaque. Transparent plates can facilitate optical monitoring of the cells in culture, and can facilitate the use of light to stimulate certain chemical or biological changes in the culture chamber or the cells.

Plates 22 and 28 may be very rigid or somewhat soft and flexible, depending on the cells to be cultured and the intended application. Rigid barriers can be used to confine cells with precision. Soft barriers can be used in applications where it is desirable to allow cells to expand or grow in size to a limited extend, such as when culturing bone cells, lens cells and other hard tissues. Cover plates may also be made of shape memory materials or photo-electric shape responsive polymers. Such cover plates may be used when it is desirable to dynamically vary the distance between barriers during cell culture, such as to periodically vary the compression or tension that a cell experiences.

While plates 22 and 28 may have various characteristics and properties as illustrated above, for a given application, the plates can be selected to have certain particular characteristics suitable for the given application and for increased control over the microenvironments of the cells to be confined within niche chamber 30.

The distance between the plates is comparable to the size of a single cell to be cultured in niche chamber 30, such that the cells grow as a monolayer in the niche chamber. As such, the distance may vary depending on the size of the cells to be cultured. In different embodiments, the distance between plates 22 and 28 may be about 0.05 to 250 microns, with the lower ranges more suitable for bacterial culture. For example to culture stem cells or stromal cells, the distance may be in the range of about 2 to 40 microns.

As will be appreciated by a skilled person, growing cells in a monolayer can be advantageous. For example, it facilitates monitoring of the cells in culture because the optical path across a monolayer can be short; direct manipulation of neighbouring cells to control the target cell's niche (e.g. by placing or removing a neighbouring stromal cell); and precise positioning of sources and sinks at the target cell.

When the gap between plate 22 and 28 is sized to confine cell growth to a monolayer, conveniently, large molecules introduced into culture chamber 26, such as growth factors or cytokines can only diffuse into niche chamber 30 at a reduced rate, compared to small molecules such as oxygen and glucose, thus creating a concentration gradient between the bulk media and cells located away from the opening between the plates. Since concentration gradients exist in vivo, it may be desirable in some applications to create such gradients in order to replicate the biological microenvironment. It has been found that when plates 22 and 28 are at a distance comparable to the size of a single cell, the resulting gradients of some large molecules can be conveniently similar to the corresponding gradients of these molecules in biological niches.

The number and size of the openings of niche chamber 30 can be adjusted, dynamically if desired, to suit specific requirements of a particular application. For instance, niche chamber 30 may be closed, or partially closed, for example by including one or more side plates (not shown). The side plates may have one or more openings thereon. A side plate may be permeable, impermeable, or selectively permeable. The opening on a side plate may have various dimensions, ranging from nanometre-scale pores to cell-scale channels that permit migration or extension of cells out of niche chamber 30.

Where no side plates are present, or where the side plates have identical openings, a symmetrical concentration gradient may be created inside niche chamber 30. By including only one side plate, or with asymmetrical openings in the side plates, a relatively long-lasting directional concentration gradient of macromolecules can be formed within niche chamber 30, such as to reproduce concentration gradients a particular cell type may encounter in vivo. Container 25 may further include a dam adjacent an opening of niche chamber 30 so as to partition the bulk media to create a strong, unidirectional concentration gradient in niche chamber 30. Both the strength and the duration of a gradient depend on the specific cellular consumption rate, the size of the diffusing molecule, the concentration of the molecule in chamber 26, and the distance between the barriers.

Plates 22 and 28 may be generally parallel or slightly angled. An angled niche chamber is desirable for creating pie-shaped niches and for encouraging cell migration along the axis of narrowing. Having a wide range of sizes in a continuous gradient within a single field of view on a microscope is efficient for evaluating the effects of a range of gap sizes on cells. For example, angles range from 0 to 45 degrees may be useful.

Apparatus 20 may be constructed using readily available materials. A standard microscope cover slip can be used as base plate 22 and a small fragment of a microscope slide can be used as cover plate 28. They may be glued together by a biocompatible elastic adhesive such as silicon glue or dental adhesive along at least two edges of cover plate 28, or at some combination of locations around the perimeter of plate 28. To form niche chamber 30 with a desired size or volume, the cover plate 28 may be separated from the base plate 22 by spacers during setting of the adhesive, or separated following setting of the adhesive if elastic glued joints are used. A tube of any desired size or shape can be constructed using standard materials for tissue culture, such as plastic, glass, or silicone, and glued over base plate 22 to form container 25.

Optionally, one or more fluid conducting tubes (not shown) may be connected to chamber 26 at various locations for communicating fluids to and from chamber 26. The tubes may extend towards, or into, the openings of niche chamber 30. The tubes may have different sizes and be separately controlled. Thus, a specific fluid content can be transported to a specific location in chamber 26 or niche chamber 30, at a specific desirable rate.

Also optionally, chamber 26 can be partitioned into two portions with a dam across the top of plate 28. When the media contained in the two partitions of chamber 26 are under different pressures or have different contents concentration, a flow through niche chamber 30 may be induced. The flow may be controlled or regulated by controlling the difference in pressure or concentration.

Figure 4:
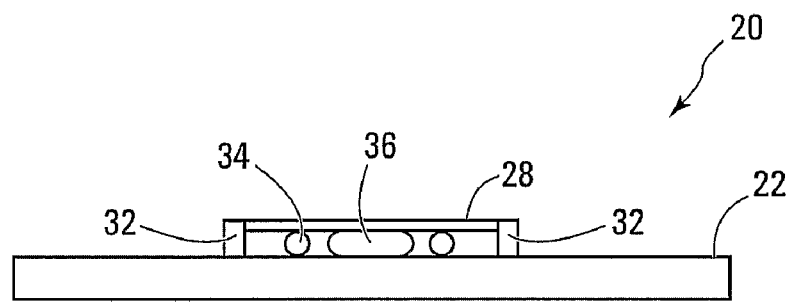
FIG. 4 is a partial front plan view of the apparatus of FIG. 1 in operation.
Figure 5:
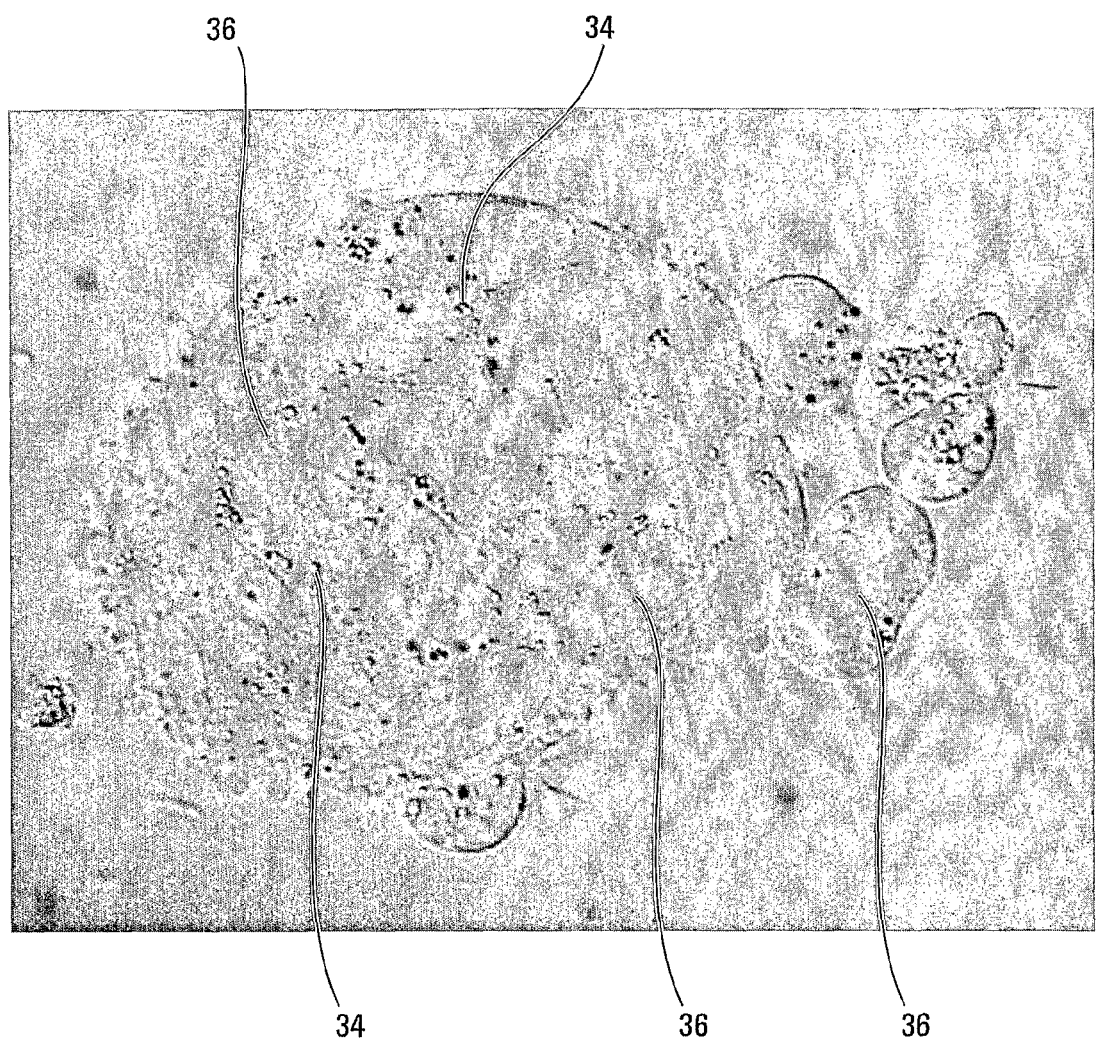
FIG. 5 is a differential interference contrast (DIC) image of cells cultured in the apparatus of FIG. 1.

In operation, and referencing FIGS. 1, 4 and 5, one or more cells 36 are seeded and cultured in niche chamber 30.

Before loading cells 36, chamber 26 and niche chamber 30 may be sterilized, for example by autoclaving or exposure to UV light.

Optionally, one or more appropriately sized rigid spacers 34 may also be placed in niche chamber 30 between plates 22 and 28, either before, during, or after cells 36 are loaded. Suitable spacers 34 include polymer, such as polystyrene, or glass microspheres. The spacers can be fluorescent. They can also be coated with biomolecules or reactive chemical functional groups. They can be magnetic. Spacers 34 should be sufficiently rigid to resist compression. Spacers 34 can facilitate positioning of plates 22 and 28 and can prevent cells in niche chamber 30 from being overly compressed so as to damage the cells.

As discussed, it is desirable to prevent plates 22 and 28 from over-compressing cells 36. The inventors have found that even if the plates were initially positioned correctly, if no preventive measures are taken, disturbances during cell culturing may cause the plates to slightly deform and thus damaging cells 36 between plates 22 and 28. In this regard, rigid spacers 34 dispersed between the plates are particularly advantageous. It has been discovered that microspheres can be used as spacers 34 to conveniently and precisely position the plates and to prevent the cells from being overly compressed. The sizes of the microspheres can be precisely controlled. The microspheres can be easily distributed, repositioned, or replaced as desired. The microspheres may be made of any biocompatible materials that are sufficiently rigid to resist movement of plate 28. As mentioned, in one embodiment, the microsphere is made of a polymer. In different embodiments, spacers 32 may also be formed integrally with one or more of the plates such as molded on the inner surface of plate 22 or 28, or on surfaces of both plates.

Spacers 34 and/or cells 36 can be loaded in various suitable manners. For instance, spacers 34 and cells 36 can be carried together or separately by a fluid into chamber 30 by injection or capillary action through one or more openings of niche chamber 30 or a tube inserted into niche chamber 30. They can also be deposited directly onto base plate 22 after removing or opening cover plate 28, Cover plate 28 can be opened slightly by separating plates 22 and 28 with tweezers and/or temporary spacers. Cells 36 can be deposited using a syringe or pipette. The pipette used may have a narrow tip, e.g. a few microns across, so that individual cells can be positioned precisely. For this purpose, the walls of container 25 may have a septum allowing access to niche chamber 30 with a syringe or a pipette.

If cover plate 28 is removed or opened during loading, it is carefully repositioned or closed after loading so as not to damage the cells.

Medium chamber 26 may be filled with appropriate culture medium. Chamber 26 can be filled either before or after loading cells 36.

Cells 36 are allowed to grow or divide in niche chamber 30 under suitable conditions, such as those described herein or as are known to persons skilled in the art.

As can be appreciated, plates 22 and 28 slightly compress cells 36, thus physically constrain cells 36 therebetween so as to keep them in niche chamber 30 and in continuous contact with each of plates 22 and 28. Cells 36 cannot travel toward or away from the plates.

Thus, cell growth within niche chamber 30 is physically confined by base and cover plates 22 and 28 to a predefined space. As the gap between the plates is generally the size of a single cell, only a monolayer of cells can grow within niche chamber 30 as shown in FIGS. 4 and 5.

As can be appreciated, since a cell 36 is confined, it is easier to control the characteristics of the cell's niche. For example, neighbouring cells of a target cell can be selectively deposited. The neighbouring cells may be of one or more particular cell types different from the target cell type. The concentration gradients of certain components of the culturing medium around the target cell can be precisely controlled. The target cell can be monitored continuously and its growth or division history can be tracked and recorded. Further, plates 22 and 28 shield cells 36 from the bulk environment and prevent cells 36 from coming into contact with foreign objects or surfaces from the top or bottom. As the characteristics of the surfaces of plates 22 and 28 can be pre-selected, it is possible to prevent exposure of cells 36 to a surface with uncontrolled or undesirable characteristics. For example, when a plate surface is selected to have characteristics mimicking those a cell may be exposed to in a biological niche, cells 36 are continuously exposed to a surface with such characteristics. Therefore, control of the microenvironment of each cell 36 can be improved. As will be understood, pre-selected characteristics of the barriers may inherently exist in the barriers or they may arise as a result of specific treatment of the barriers.

When a monolayer of cells is cultured as described above, it is possible to remove a particular cell from the monolayer of cells without significantly disturbing the neighbouring cells. As will be understood by persons skilled in the art, removal of a particular cell may be desirable, for example, when the particular cell is observed to meet one or more criteria which may be related to karyotype, morphology and cell size.

As can be understood, one or more cells 36 can be cultured while the movement of the cell(s) is restricted such that each cell 36 is in continuous contact with two opposing barrier surfaces. However, each cell, or the cells as a whole, is mobile between the barrier surfaces, i.e. movable in a direction generally parallel to the barrier surfaces. Conveniently, the cell(s) can be imaged during culturing using a non-confocal imaging device, such as a bright field imaging device or a fluorescent imaging device including a differential interference contrast (DIC) imaging device. High resolution images can be obtained without using a confocal microscope because the cell(s) can be confined within the proximity of the focal plane of a non-confocal imaging device. Thus, cell(s) 36 can be monitored, including imaged, over a long period of time (up to many days) without being significantly adversely affected.

The gap between the plates 22 and 28 may be increased to allow multiple layers of cells to grow between the plates without losing sufficient control over the individual niches and therefore the control of characteristics of an individual cell. In most embodiments, the number of cell layers will typically not exceed 4 or 5. For example, the gap may be comparable to the total size of two cells. Further, as mentioned, the inner surfaces of plates 22 and 28 may have different affinities to different type of cells. As can be appreciated, in such a case, it is possible to culture two layers of cells between plates 22 and 28 with the first type of cells in one layer and the second type of cells in another layer. The cells of the two layers may interact as they normally do in natural environments.

The number of cells 36 in culture chamber 30, or the number of cells surrounding a particular cell 36, can be limited by the use and positioning of plates 22 and 28. Limiting the number of cells can serve various purposes such as to permit control of properties of individual cell(s) or to allow improved monitoring of the cultured cell(s).

Figure 6:
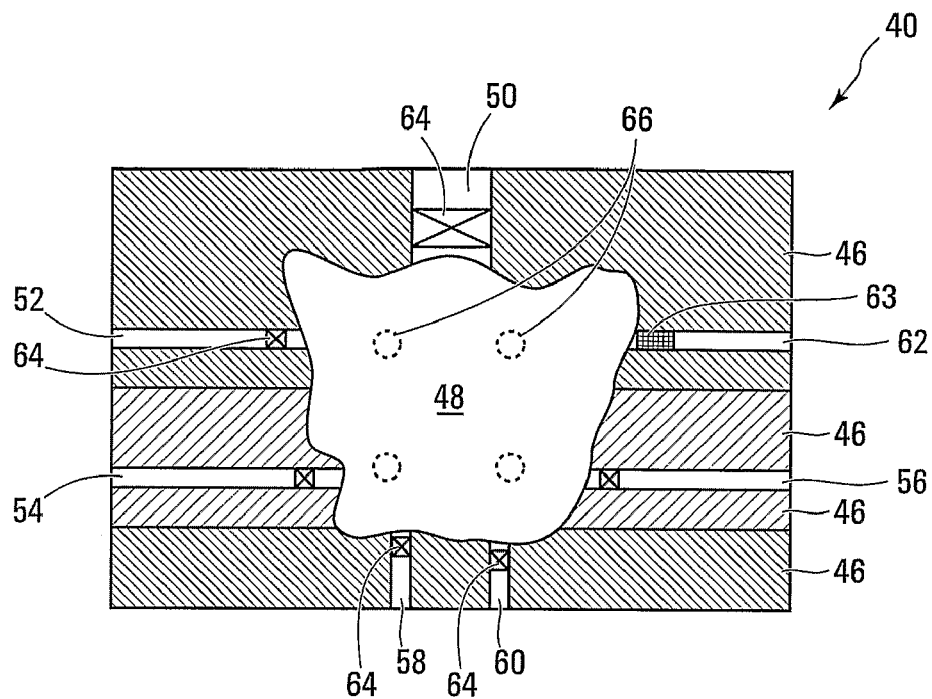
FIG. 6 is a schematic top cross-sectional view of a cell culturing apparatus according to another embodiment of the invention.
Figure 7:
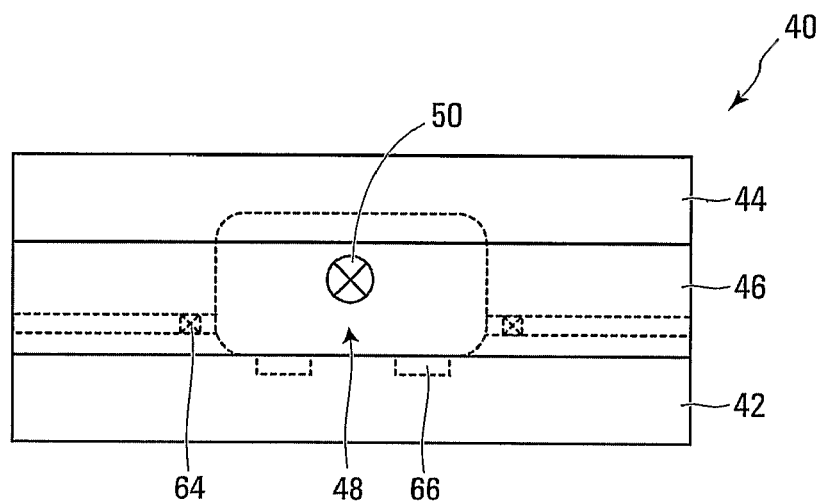
FIG. 7 is a schematic front cross-sectional view of the apparatus of FIG. 6.

FIGS. 6 and 7 schematically illustrate another exemplary embodiment. Cell culturing apparatus 40 has a base plate 42, a cover plate 44, and a number of sidewalls 46, which together define a niche chamber 48.

Base and cover plates 42 and 44 are positioned opposite each other at an appropriate distance. The distance is comparable to the size of the cells to be cultured. The inner surfaces of plates 42 and 44 may be generally flat or contoured. In cases where a number of cells having different sizes are to be cultured, the distance between plates 42 and 44 may be either comparable to the size of the largest cell, or varied so as to accommodate differently sized cells at different locations. As an example, a minimum distance of 8 microns may be adequate for culturing sperm cells.

Sidewalls 46 are sandwiched between the base and cover plates 42 and 44 and are positioned to simulate desired in vivo cell boundaries. The distance between each pair of opposing sidewalls 46 may vary depending on the application, as can be appreciated by persons skilled in the art. For example, for culturing sperm cells, the distance between sidewalls may vary from 30 to 80 microns.

One or more inner surfaces of chamber 48 may be shaped to simulate the shapes of interfaces in biological niches. One or more of the inner surfaces may be non-adherent to the cells to be cultured. One or more of the inner surfaces may be coated with materials such as extracellular matrix proteins, gels, proteoglycans, and growth factors so as to induce cell adhesion or other cellular response.

Apparatus 40 also has a plurality of fluid conduits for communicating a fluid to and from chamber 48, which includes delivery channel 50, source channels 52, 54, 56 and 58, and sink channels 60 and 62. Cells may be delivered to chamber 48 through delivery channel 50 using a carrier fluid. Culture fluid containing growth media may be supplied to chamber 48 through source channels 52, 54, 56 and 58. The fluid may include nutrients, dissolved gas, pharmaceutical compounds, tracer dyes, magnetic particles coated with various molecules such as antibodies, soluble molecules including molecules normally secreted by the cells to be cultured, solid or phase-distinct matrix coated with specific effector molecules, and the like. Fluid inside chamber 48 containing materials such as carrier liquid, unconsumed growth media, wastes, debris of dead cells, and the like may be extracted from chamber 48 through sink channels 60 and 62. As can be appreciated, the number of conduits or channels may vary depending on application and manufacturing considerations. For example, a single channel may serve alternatively both as a source and a sink channel.

The construction details of the channels can vary depending on the functions to be performed in a particular application. A brief description of possible structures of the channels is given below for illustration purposes.

The sizes of the channel cross-sections can vary depending on the required flow rate of the carrier fluid. Thus, they may be calculated from the desired amount of fluid contents, such as nutrients or other media content to be supplied to cells in chamber 48, or wastes and debris produced in chamber 48 that need to be carried away. For example, for culturing sperm cells, a source channel can be structured to simulate the blood supply by a capillary. The source channel may have a 10 micron diameter cross-section allowing flow rate to vary between 1 to 100 microns per second, which is sufficient to supply enough oxygen to, e.g. 10 cells. As another example, to culture a sperm cell, source and sink channels may be used to supply and withdraw seminiferous tubule fluid which flows across the flagella of the immature sperm providing nourishment and allowing them to develop correctly. In an exemplary construction, a flow rate of one picoliter per second may be required, which can be varied during the culture to simulate in vivo variation. Thus, sink and source channels 10 microns in diameter may be appropriate. In another example, to simulate the presence of cells that would be present in vivo but are not in the niche chamber 48, sink and source channels may be used to provide and withdraw a fluid containing cells, e.g. cytokines. In this case, the flow needs only to be intermittent and at a low rate, such as on the order of femtoliters per second. Thus, the channels can have a round shape with a 2 um diameter.

A filter or permeable membrane 63 may be installed at the interface between a channel (e.g. channel 62 as shown in FIG. 6) and chamber 48 so that the flow rate can be precisely controlled or regulated, or to allow only selective substances in the fluid to pass through.

A valve 64 may be installed in a channel to regulate or control the fluid flow in the channel. Each channel may have a control valve 64. Valves 64 can be of different types depending on the particular application. Valves can be of the simple hydraulic type in which an accessory channel is pressurized to deflect a membrane to block off a channel, the thermal type in which a gas is heated to distend a similar membrane, the hydrogel pH-controlled type (the pH is applied through an accessory channel) in which a hydrogel changes volume dramatically with pH blocking a channel, or other suitable types. Exemplary valve designs are described in "Monolithic microfabricated valves and pumps by multilayer soft lithography," *Science* 288 (2000) 113-116, M. A. Unger et al.; "Flow control valves for analytical microfluidic chips without mechanical parts based on thermally responsive monolithic polymers," *Analytical Chemistry,* 75 (2003) 1958-1961, C. Yu et al.; and "Responsive biomimetic hydrogel valve for microfluidics." *Applied Physics Letters* 78 (2001) 2589, Q. Yu et al.; the contents of each of which are incorporated herein by reference.

One or more sensors 66 may be mounted on base plate 42 (or alternatively on cover plate 44) for monitoring purposes, as will be described further below. Various types of sensors may be used. For example, biocompatible ion-sensitive field effect transistor (ISFET)-based sensors may be used to measure oxygen concentration and pH values; Clark-type amperometric biosensors may be used to detect glucose concentrations and gradients. A review of chip-based biosensors is provided by Brian R. Eggins in *Chemical Sensors and Biosensors*, John Wiley & Sons, 2002, the content of which is incorporated herein by reference. Sensors 66 may have various sizes and shapes. Sensors having sizes below 3 microns are suitable in certain applications. As will be understood by persons skilled in the art, sensors 66 may include sensors for sensing molecular concentration, temperature, osmolarity, pH, shear force, or the like. Such sensors are known to the art and can be readily obtained or manufactured.

Apparatus 40 may be fabricated by sandwiching a substrate plate between base plate 42 and cover plate 44. The substrate may be embedded with a microfluidic network with fluid channels and valves. Apparatus 40 may also have transparent indium-tin oxide conductors connected to vertical connecting wires that transverse the microfluidic network on the substrate. Networks can be produced in various manners known to a person skilled in the art, such as is described in "Three-dimensional micro-channel fabrication in polydimethyl-siloxane (PDMS) elastomer," *Journal of Microelectromechanical Systems* 9 (2000) 76-81, B.-H. Jo et al.; "Rapid fabrication of hot embossing tools using PDMS" in *Microfluidics, BioMEMS, and Medical Microsystems, Proceedings of The International Society for Optical Engineering* 4982 (2003) 110-119, J. Narasimhan and I. Papautsky; "Near-field subwavelength micropattern generation. Pipette guided argon fluoride excimer laser microfabrication." *Journal of Applied Physics* 72 (1992) 4379-4383, M. Rudman et al.; and "Dynamic mechanical properties of UV-curable polyurethan acrylate with various reactive diluents." *Journal of Applied Polymer Science* 60 (1996) 2113-2123, B. Nabeth et al.; the contents of which are incorporated herein by reference.

The network can be made by microstamping PDMS, hot-embossing, silicon micromachining, laser ablation, or UV curing such materials as isobomyl acrylate (IBA). PDMS is the preferred material, and standard microfabrication techniques can be used to create molds that are used to cast layers of PDMS that have imprinted on their surfaces the various channels surrounding chamber 48. The PDMS layers are assembled one on top of the other to build up sidewalls 46 by methods known to those skilled in the art. Alternating layers of PDMS are made with excesses of one and then the other of the two components that are mixed to form PDMS. After curing, adjacent layers are fused by heating them so that the excess component in one layer reacts with the excess component in the sandwiching layers.

The material of each sidewall 46 (hence its properties) may be individually and specifically selected to produce a desired specific effect or to prevent an undesired specific effect. For example, to replicate the in vivo niches for the stem cell, spermatogonia and their supporting Sertoli cells, sidewalls can be derivatized with collagen-IV and/or laminin-1. Laminin-1 is suitable because laminin is the predominant component of the basal lamina which borders spermatogonia cells in a biological niche. Collagen-IV gel is suitable because male germline stem cells do not bind as strongly to collagen-IV such that walls made of collagen-IV gel should facilitate controlling the orientation of the cells growing in chamber 48. The collagen-IV gel may be derivatized with binding proteins normally found on the membranes of cells to which the Sertoli cells are exposed in biological niches, such as claudin, occludin, cadherins, connexins, and selecting. The remaining inner surfaces of chamber 48 may be made of biologically inert materials such as glass or polydimethylsiloxane (PDMS).

Sidewalls 46, particularly their contoured inner surfaces, may be shaped using standard micromachining techniques well known to those skilled in the art, such as is described in *Handbook of Microlithography, Micromachining, and Microfabrication,* 1997, Vols. 1 and 2, The International Society for Optical Engineering, P. Rai-Choudhury (Editor), the content of which is incorporated herein by reference.

Apparatus 40 may be made of transparent materials to facilitate transmitting light through chamber 48 so that the cells may be monitored optically, or light can be used to initiate specific photochemical reactions within chamber 48.

Apparatus 40 may also incorporate other physical, chemical, or electronic components necessary or desirable for a given objective of the cell culture. For example, it may be connected to other apparatus and instruments for proper operation of the culturing processes, as would be apparent to and understood by a person skilled in the art of bioprocess engineering, such as is described in *Biochemical Engineering,* 1997, Marcel Dekker Press, H. Blanche and D. Clarke.

A control system such as a computer or other automation devices (not shown in the figures) may be used to monitor and control the operation of apparatus 40, and to analyse obtained data. The culturing environment in chamber 48 may be adjusted dynamically based on the information gathered in real time. Media flow and metabolite concentrations can be monitored and controlled. For example, sensors 66 may be connected to the control system using transparent electrodes and may be used to simultaneously measure the concentration of oxygen and the pH value in chamber 48. Further, with multiple sensors 66, the gradient of a given material in the chamber can be measured. Feedback information may include values of pH, glucose and oxygen concentrations, temperature, osmolarity, share forces in chamber 48.

Microfluidic pumps (not shown) may be connected to the channels to propel a fluid into and out of chamber 48. Any suitable pumps may be used. Exemplary pumps are described in "A ferrofluidic magnetic micropump," *Journal of Microelectromechanical Systems* 10 (2001) 215-221, A. Hatch et al.; "Micromachined flow handling components—micropumps", *Proceedings of SPIE—The International Society for Optical Engineering* 3857 (1999) 52-60, O. Soerensen et al.; and "Micropumps—Summarizing the first two decades," *Proceedings of The International Society for Optical Engineering,* 4560 (2001) 39-52, P. Woias; the contents of which are incorporated herein by reference. Examples of suitable pumps include a ferrofluidic slug propelled by a rotating magnet around a ring chamber, piezoelectric crystal doors that seal against a soft jamb, piezoelectric crystal pumps, or other types. Transverse electrokinetic pumps may be used. Flow rates under electrokinetic pumps can reach tens or hundreds of microns per second in channels with cross-section sizes ranging from 0 to 1000 microns. The pumps may be placed at various points in the network of channels connected to chamber 48 to overcome flow resistance, particularly in long channels.

The surfaces of chamber 48 may be given a positive or negative charge prior to loading of cells to control cell attachment or behaviour. The charge may be conferred by various means known to those skilled in the art, for example exposure to oxygen gas at 400° C., exposure to acids or bases, or rubbing with materials with differing electron affinity.

The inner surfaces of chamber 40 may be made reactive so that other molecules may be covalently linked to it. The surface can be made reactive in various ways known to those skilled in the art, for example by treatment with such molecules as aminopropyltrimethoxysilane (APTS), which presents amine groups on the surface. Thin layers or bulk materials may be linked to the surface. Bulk materials include gels made from protein, polyacrylamide, or other materials. Such gels may be formed in moulds made with standard microfabrication techniques. The gels are placed on the sidewalls and covalently bound into place by reaction with the activated surfaces. For example, collagen-IV gels or fibronectin may be used. Since male germline stem cells do not bind as strongly to collagen-IV or fibronectin as they do to laminin-1, when some surfaces of chamber 48 are coated with collagen-IV gels or fibronectin and other surfaces are coated with laminin-1, the cells in the chamber may be oriented as desired.

The surfaces may be derivatized with binding proteins that a target cell type is normally exposed to in a natural environment, such as claudin and occludin (for tight junctions), cadherins (for actin-linked, adherens junctions), co unexins (for gap junctions), and selectins (for selectin-lectin interactions)). Thin layers of proteins may be patterned on the inner surfaces of chamber 40, for example by treatment of the APTS-treated surface with glutaraldehyde, or with the photoactivatable cross-linker 4-benzoylbenzoic acid succinimidyl ester, or by using other techniques known to those skilled in the art as described in "Surface micropatterning to regulate cell functions," *Biomaterials,* 20 (1999) 2333-2342, Ito and Yoshihiro, and references therein, the content of which is incorporated herein by reference. The proteins may be of any type. As an example, for culturing sperm cells, laminin-1 may be used since laminin-1 is the predominant component of the basal lamina in in vivo niches of sperm cells. The proteins may be patterned in concentration gradients on niche-bounding surfaces by methods known to those skilled in the art.

Electrical conductors (not shown) may be embedded in apparatus 40 for connecting sensor and pump electrodes to external electronics and power sources. The conductors can be deposited using standard microelectronics fabrication techniques. For example, the conductors may have a thickness on the order of nanometers. A conductor may run along the surface of a substrate or through the substrate. Conductors may also be covered with inert coatings with non-conducting materials such as aluminium oxide.

Niche chamber 48 may be useful for culturing cells of particular types, e.g., cells found in mammalian testis. As will be described, chamber 48 may be used to culture an assembly of cells, each having its respective, individually controlled niche, where the assembly together produces a desired biological effect or product such as a sperm.

An exemplary process of constructing apparatus 40 is as follows:

prepare a generally flat substrate made of silicon or silicon dioxide, which forms base plate 42;

embed sensors 66 on base plate 42;

lay down indium tin oxide or titanium nitride transparent conductors (not shown) connecting sensors 66 to electrodes on the exterior surface of base plate 42;

deposit an insulating layer (not shown) on top of the conductors, where the insulating layer may be made of, for example, silicon nitride, polyimide, or polysiloxane;

construct sidewalls 46 with microfluidic networks by creating and stacking several layers of substrate, each with channels moulded into its surfaces, as described above;

cover the sidewalls 46 with a generally flat substrate, which forms cover plate 44, thus forming chamber 40;

optionally, and either before or after covering chamber 40, make some inner surfaces of chamber 40 reactive so that certain molecules may be covalently linked to it;

optionally, and either before or after covering chamber 40, pattern thin layers of proteins on some inner surfaces of chamber 40.

In operation, a number of desired seeding cells are deposited in chamber 48. Base and cover plates 42 and 44 confine the cells therebetween so as to limit the cell movement towards or away from the base and cover plates.

Figure 8:
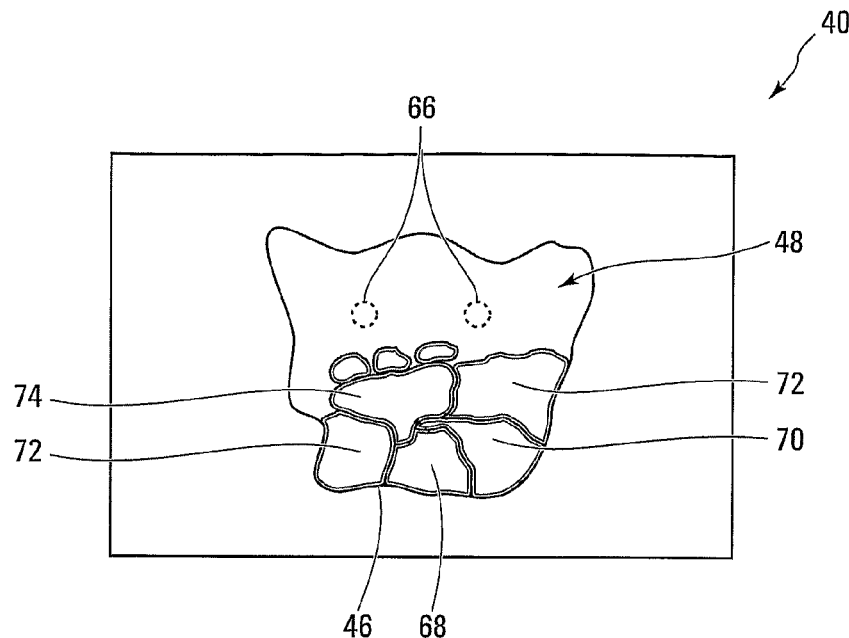
FIG. 8 is a schematic top plan view of the apparatus of FIG. 6 in operation.

As illustrated in FIG. 8, to further confine a target cell 68 or to provide a desired microenvironment for target cell 68, one or more other cells (e.g. cells 70, 72 and 74) may be disposed around target cell 68 within chamber 48. In such cases, the other cells also help to confine a target cell. The target cell and the neighbouring cells may be manually specifically positioned in chamber 48, or they may position themselves through self-organization. As can be appreciated, two adjacent cells can mutually constrain each other when they are compressed towards each other. A target cell can thus also help confining its neighbouring cells.

Cells may be seeded into chamber 48 by deposition with a micropipette from the top with cover plate 44 removed. Cover plate 44 may be lowered into position slowly so as not to disturb the cells. Cover plate 44 may be positioned with standard positioning tools. Cells may also be seeded through one or more of the fluid channels 50 to 62. For example, cells may be delivered to chamber 48 via one of channels 50. Carrier fluid may be removed through channel 62 by opening valves 64 in channels 50 and 62. Once delivered, cells may self-organize or self-assemble in chamber 48, which can be facilitated by the barrier surfaces present in chamber 48 which can have pre-selected suitable characteristics such as appropriate affinities to specific cells.

After seed cells are loaded, valve 64 in channel 50 may be closed.

Chamber 48 receives fluid culture media through channel 52. For example, for culturing spermatogonium, the suitable media may contain seminiferous tubule liquid substitute. The media may have high concentrations of amino acids, potassium, androgens, and estrogens. As can be understood, these media simulate the liquid in the seminiferous tubules that is needed for proper development of sperm flagella.

Carrier fluid may be drained from channel 62.

Supplement culturing media is communicated to chamber 48 through channels 58 and 60, which serves as source and sink channels respectively. For example, the supplement media may include testosterone which is normally present in organisms on the side of a basal lamina opposite the tubule lumen.

The media flow and concentrations can be monitored and controlled. For example, sensors 66 may be used to simultaneously measure the concentration of oxygen and the pH value in chamber 48. Further, with multiple sensors 66, the gradient of a given material in the chamber can be measured.

When apparatus 40 is transparent, cell growth in chamber 48 can be monitored, for example, by using microscopic imaging devices. For example, such devices may be used to detect the presence of mature sperms, i.e., sperms that can be removed and used for the intended applications.

A computer or other automation devices may be used to monitor and control the operation of apparatus 40, and to analyse obtained data. The culturing environment in chamber 48 may be adjusted dynamically based on the information gathered in real time. Feedback information may include values of pH, glucose and oxygen concentrations in chamber 48.

FIG. 8 illustrates a particular example of cells cultured in apparatus 40. As illustrated, chamber 48 contains a type A pale spermatogonium 68, a type B pale spermatogonium 70, and two Sertoli cells 72. While not shown, it can be appreciated that each cell is constrained by base and cover plates 42 and 44 therebetween.

As can be seen and appreciated by a person skilled in art, the niche for each cell grown in chamber 48 resembles the biological niche for such a cell. Each cell is confined by one or more other cells, and, in some cases, one or more sidewalls 46. For example, cell 68 is confined by cell 70 and 72 in the horizontal direction and by a wall 46 and cell 74 in the vertical direction. In other words, cell 70 and 72 confine cell 68 therebetween and they contact cell 68 on opposite sides and prevent cell 68 from travelling away from them; likewise, cell 74 and the bottom sidewall 46 also confine cell 68 therebetween and contacting cell 68 on opposite sides to prevent cell 68 from travelling away from them.

Cells in chamber 48 receive nutrient by diffusion through spaces between cells and, to a lesser degree, through cells. Nutrients may also be provided through channels located above or below a cell.

If desired, cells may be removed from the culture chamber. To remove a cell or cells such as a sperm from chamber 48, channel 50 is opened temporarily so that the cells can be carried by a fluid carrier out of chamber 48.

One of the walls of apparatus 40 may have a septum allowing access to chamber 48 with a syringe or a micropipette.

Apparatus 40 can be used in various applications.

For example, apparatus 40 can be used to produce healthy sperm with a male subject's genetic profile in the event of, for example of testicular cancer or infertility. Spermatogonium cells may be taken from a healthy subject and preserved for controlled growth at a later time as described herein.

In organisms multiple cell types often exist together in multicellular units to perform a specific function, and these units often form a physically distinct assembly of niches. As can be appreciated, apparatus 40 may be used to provide and control an assembly of artificial niches.

Apparatus 40 may also be used to provide a single niche for a single cell, or niches for part of a multicellular unit. For example, in the case of culturing sperm cells described above, instead of seeding the Sertoli cells, apparatus 40 may be configured and controlled to provide important proteins such as Sry, inhibin, and androgen-binding proteins that are produced by Sertoli cells and the boundary walls similar to those created by Sertoli cells to establish the blood-testis barrier.

As can be appreciated, an array of apparatus 40 can be fabricated on a single device. As illustrated, chamber 48 can accommodate multiple cells or it may be designed to culture a single target cell.

Further specific exemplary embodiments are described below.

(i) Automated Monitoring and Control

As mentioned earlier, computers and computer programs can be used to control the culturing and monitoring of cells and to analyze obtained data. Microprocessors can be incorporated into a culturing device or in a separate centralized unit. The computer system can record the measurements from the sensors, analyze the data, and control the niches accordingly. The niches and accessory devices may be monitored and controlled by one or multiple processors and software programs.

Figure 9:
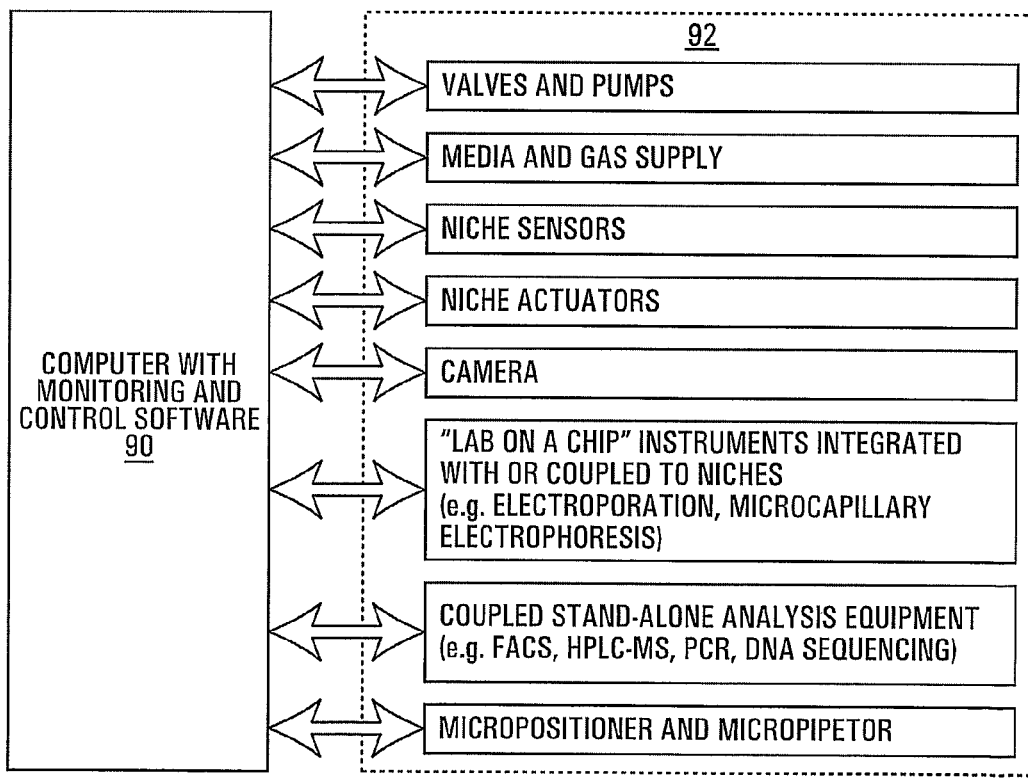
FIG. 9 is a schematic block diagram showing data pathways between a controlling system and a cell culturing and analysis system, exemplary of an embodiment of the invention.

FIG. 9 illustrates an exemplary configuration of data pathways between the computer system 90 controlling culturing and the controlled culturing and analytical systems 92.

The niche enclosures may be included in a mobile cartridge that has openings, electrical contacts, mechanical connectors, and other features on the outer surface for interfacing with other devices. For example, the cartridge can be plugged into a device that performs routine culturing functions that can be centralized at a place distant from the immediate vicinity of each niche assembly. Such functions include the storing of nutrients and gases, supplying positive or negative pressure to move the liquids, solids, or gases, receiving and analyzing signals from sensors in the niches. The device can have a multi-well plate and a cartridge can be placed in each well. Alternatively, the cartridge can be placed in a biosensor device, for example, one that shines light through niches to determine if a cell is expressing a specific reporter gene. The cartridge can be provided preloaded with cells. In further alternative, the cartridge can be placed on a microscope stage or in a multi-well plate.

(ii) Conducting Cell-Scale Molecular Biology in a Single Controlled Niche

The tools of molecular biology can be applied to cells in artificial niches. This has multiple benefits. The cells are in a known state and a defined environment. The cell culturing device provides an "operating room" for a cell, by providing life support to the cell to allow cells to survive traumatic treatment, holding the cell in place, and allowing fine control of treatments such as microinjection or electroporation. The culture device can contain a single niche or a few niches.

A cell culture apparatus or device exemplary of the invention may be used to perform single-cell molecular biology, chemical analysis or other manipulation, on an individual cell in a defined and appropriate microenvironment.

Figure 10:
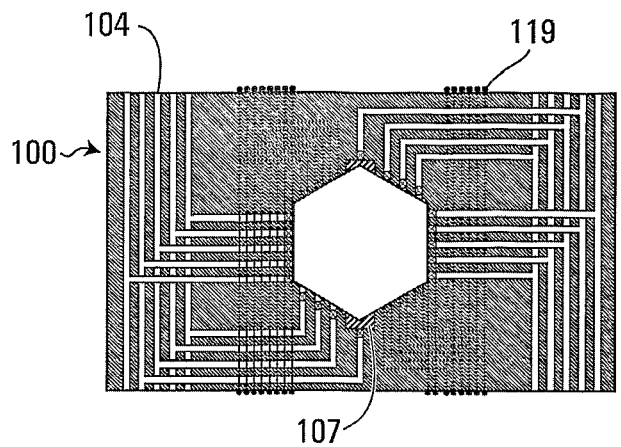
FIG. 10 is a schematic top view of a cell culturing apparatus according to a further embodiment of the invention.
Figure 11:
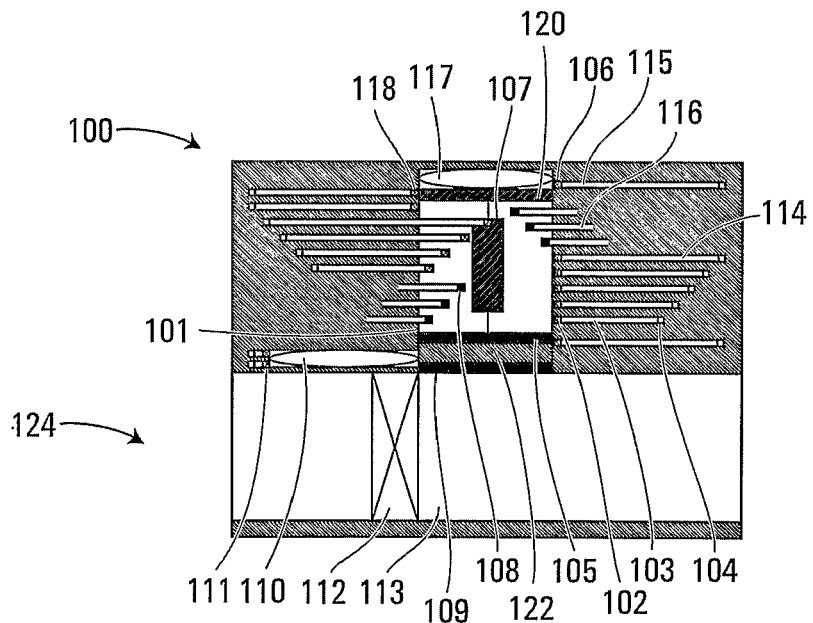
FIG. 11 is a schematic front view of the apparatus of FIG. 10.

FIGS. 10 and 11 illustrate a culturing device 100 defining a niche chamber. The niche chamber has a pre-defined shape and size for accommodating only one to three niches in at least one dimension.

The niche chamber has interior surfaces 101 and is connected with multiple microfluidic channels 103 regulated by valves 102. Different channels 103 may used for delivering to or extract from the chamber different solutions or materials and may have different sizes and shapes. Channels 103 may be interconnected with adjacent cell culturing units through channels 104. Channels 103 and 104 allow vectors, antibodies, calcium chloride, lipofectin, or any other reagents to be introduced and the media to be flushed for cell washing. The supportive niche environment is established by anisotropic, biomimetic extra-cellular matrix coatings on the surfaces that can remain in contact with a cell during handling, suitable sources and sinks of solutions, and suitable size and shape of the niche chamber.

Cells are loaded and unloaded through microfluidic channel 113 via valves 112 and 124 while withdrawing solution through channels 114 and 104. Valve 124 includes a slider 122 slidably mounted between plates 105 and 109. Plates 105 and 109 each has a through hole (not shown) for allowing access to, and/or fluid communication with, the niche chamber. Slider 122 can slide in and out between plates 105 and 109 to close or open the through holes. Slider 122 is actuated by bladder 110, which is in turn controlled by valve 111. Gels or filters 107 allow diffusion of solutions to mimic natural bathing of the cell. Cells can also be introduced by deposition through the top or bottom of the niche chamber with a micropipette, or through channels passing through e.g. plates 105 and 109.

Electrodes 108 allow an electric field to be established across a cell for electroporation. Electrodes 108 are placed on opposite sides of the cell so that the cell in the niche can be electroporated. Traditional electroporation results in a high level of cell death because the cell membrane is compromised. In an artificial niche controlled in a manner as described herein, the cell can be supported on all of its sides. This could be used for the transfection of cells with controlled copy number because a single vector can be placed in the immediate vicinity of a single cell, rather than having to rely on chance to bring these two together in a bulk solution.

Piston 120 can be provided and so disposed that it can slide within the chamber so as to change the volume of the chamber, for instance under pressure of bladders 117, the expansion and contraction of each of which is in turn controlled trough channel 115 and valve 106.

As can be appreciated, the volume of the niche chamber in device 100 can be varied by other types of actuators than an inflatable bladder. For example, piston 120 can be actuated by other known actuating mechanisms. As an example, it can be attached to a plate that can be moved up and down by macroscopic means such as screws, levers, clamps, micrometers, piezoelectric crystals, or the like.

For example, expanding bladder 117 can cause piston 120 to compress a cell in the chamber to rapture so that, for example, its contents can be sampled using channels 114 for analysis by microcapillary electrophoresis, RT-PCR, or other methods, in some cases at other locations on the same monolithic device 100. Cultured cells can be compressed or exposed to other treatment, that bursts them, and their contents can be transported to an analysis device such as microcapillary electrophoresis, single-celled mRNA extraction, HPLC-mass spectrometry, and other analytic tools, through a microfluidic channel.

Cultured cells can also be compressed toward each other so as to enable fusion of the cells. Fusion of cells may be desirable, for example, in hybridoma production. Expanding bladder 117 can cause two cells to be compressed together as the volume available is decreased as the piston 120 presses down a movable niche barrier. Chemicals for fusion such as polyethylene glycol or for bursting cells such as high salt solutions can be added through the channels.

Figure 12A:
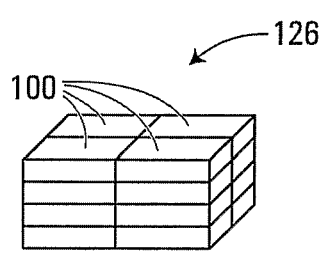
FIG. 12A is a schematic perspective view of an assembly of a plurality of cell culturing apparatus.
Figure 12B:
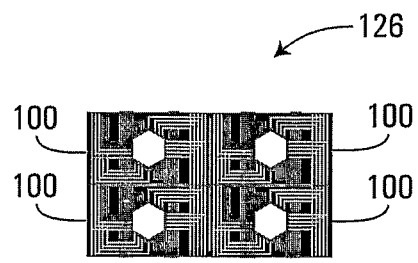
FIG. 12B is a schematic top plan view of the assembly of FIG. 12A.

Culturing device 100 may be integrally formed with other devices such as other embodiments of the invention in a single apparatus. For example, as illustrated in FIGS. 12A and 12B, an assembly 126 of devices 100 may be provided. In alternative embodiments, an assembly may also include one or more of the other embodiments described herein. The unit devices, such as device 100, may be stacked together with or without spacers and with or without layers of gas and/or media in between. As illustrated, each unit device may be generally plate-shaped and the units may be stacked in parallel. The individual culturing units may be arranged into 2D and 3D arrays. Slots and grooves or other intersecting forms on adjacent devices may be used to align the devices. Channels 104 and electrical contacts 119 can connect with their counterparts on adjacent devices.

Microfluidic channel openings can be in contact with a cultured cell to allow patch clamping of the cell to detect ion channel function.

Microfluidic channels allow niche contents to be sampled and fed to devices that perform such analyses as microcapillary electrophoresis, gas chromatography, high pressure liquid chromatography, mass spectrometry, or other measurements.

Fluid in a fluid channel 104 connecting two or more niche chambers can be sampled for analysis by High Performance Liquid Chromatography (HPLC)-mass spectrometry, microcapillary electrophoresis, or other analytical tools.

(iii) 3D Tissues

A shortcoming of existing artificial organs is that they lack fine structures. For example, existing artificial skins lack hair follicles and sweat glands and are therefore uncomfortable and appear unnatural.

Figure 13:
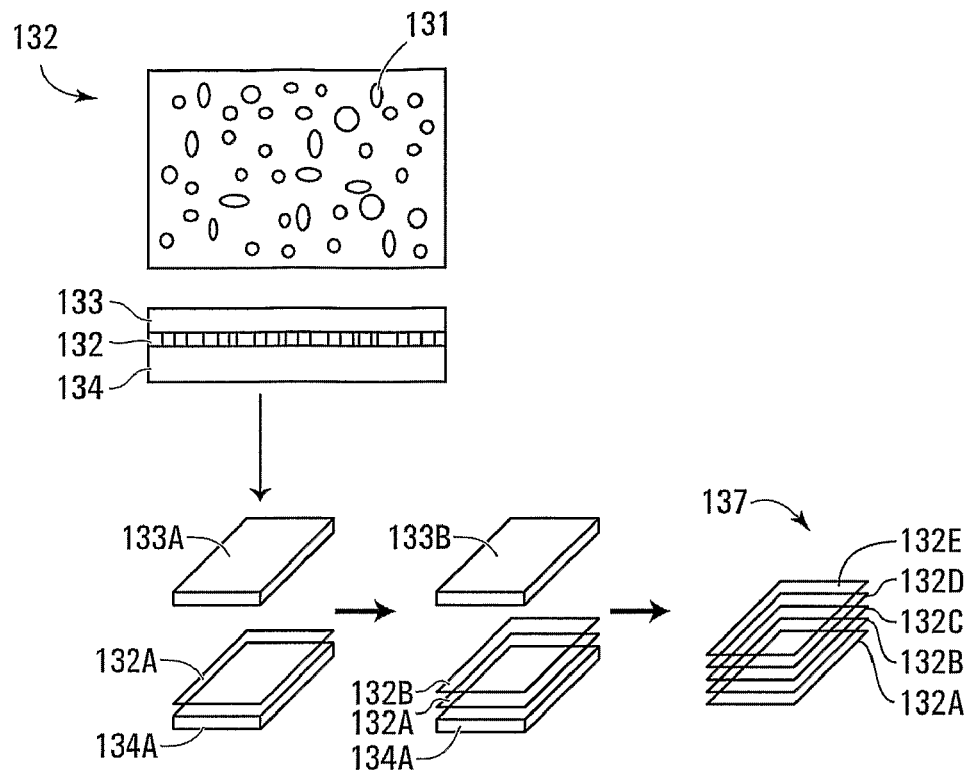
FIG. 13 is a schematic diagram illustrating the formation of an assembly of cells, exemplary of an embodiment of the invention.

FIG. 13 illustrates a procedure for assembling cells in a three dimensional (3D) pattern exemplary of an embodiment of the invention. A plurality of artificial niches 131 are formed in a two-dimensional (2D) layer 132. Several such layers 132 may be formed and cultured. Each layer 132 may contain different niches 131 for culturing different cell types, arranged in natural 2D patterns of the cells to be cultured. Cells cultured in different layers 132 may have different cell types or patterns and are grown separately. Layers 132 can be stacked together to form artificial skin 137 that has the same 3D pattern of cells found in natural skin.

In an exemplary embodiment, cells in several patterned layers 132 are grown independently, where each layer 132 corresponds to a layer of cells in the target tissue type. The pattern of niches for the cells is made to correspond to the pattern of cell types found in a single-cell-thick or few-cell-thick layer of the skin. Each layer of cells may be cultured in confinement between a top barrier 133 and a bottom barrier 134. Top and bottom barriers 133 and 134 present the cells with the niche components that similar natural cells would normally be exposed to by the layers of cells above and below them in their natural tissue. The top and bottom barriers 133 and 134 may also interconnect to form niche boundaries laterally within the layer.

To form an artificial skin tissue 137, a foundation layer 132A, which may correspond to a layer of hypodermis, is first chosen. The top barrier 133A can be removed to expose the cells in niches 131. As can be appreciated, when top barrier 133A is removed, niches 131 are exposed but can still be fed from the bottom. A layer 132B, which for example corresponds to a layer of dermis, is then laid on top of layer 132A. The bottom barrier 134B for layer 132B may be treated to minimize cell attachment, for example by brief introduction of an extracellular matrix (ECM) protease on one side of the cells. After removing the top barrier (not shown) covering layer 132B, layer 132B may be ejected from bottom barrier 134B by pressuring the underside of each cell through a microfluidic channel (not shown). To add another layer 132, bottom barrier 134B is removed. The process can be repeated to add additional layers. Stacked layers 132 can be glued to each other with biological adhesives such as those commonly used in surgery. This process of depositing and attaching successive layers is repeated until the stacked layers forms an artificial skin tissue 137 resembling the 3D organization of a natural skin tissue. Structures that run vertically through the natural tissue such as blood vessels and follicles are grown piecemeal in the separate layers 132 until the layers are aligned and stacked, when the cells in tissue 137 can adhere to each other to form the structures.

Islands of vascular epithelial cells can be cultured to facilitate angiogenesis and integration with the host vascular system. Thus, blood vessels can quickly form and begin feeding the assembled tissue 137. Vessels that traverse adjacent layers can be created by growing rings of endothelial tissue that align in successive layers. Nerves can also be patterned. Neurons whose bodies are placed around the edge of a layer with axons extending into the layer may obviate the need for innervation after organ synthesis. Fine features such as hair follicles that are not recreated in current tissue engineering technologies may be reproduced in this way.

Layers of biodegradable polymers such as polylactic or polyglycolic acid or layers of extracellular matrix material such as collagen sheets with appropriate holes can be laid down on and attached with surgical glue to the top of a layer 132 before stacking it to give the layer cohesiveness.

Some niches may be designed so that their cells connect adjacent niches with extracellular matrix materials through channels that will be opened on the top when the top barrier 133 is removed.

(iv) In vitro Fertilization

An ovum can be grown in an artificial niche in a state optimized for in vitro fertilization. A micropipette tip can be introduced to the niche and the ovum microinjected. The niche may expand to accommodate divisions of the ovum.

(v) Long Term Preservation of Cells (Cell Banks)

Currently the most common method of preserving cells for later use is to freeze them. A disadvantage of freezing is that the cells are exposed to an unnatural environment, which may cause undesirable effects such as high death rate.

Cells cultured in individually controlled artificial niches can be maintained in a specific state for a long period of time. The metabolism of the cells may be slowed down, for example, by maintaining them at a low temperature above freezing point. The cells may be protected from cosmic rays by shielding. Surfaces bordering an artificial niche can be selected to maintain the cell (such as a stem cell or a progenitor cell) in an undifferentiated state. For example, differentiation may be reduced or controlled by preventing cell attachment to the barriers.

(vi) Producing Cell-Derived Products

In traditional bioreactors used for producing recombinant proteins and other biomolecules, it is known to those skilled in the art that toxic conditions can exist that are detrimental to cells, with the result of a reduction in product yield. Common toxic conditions include accumulation of ammonia, lactate, or ethanol; insufficient or excess oxygen; lack of glutamine, glucose, or growth factors; low or high pH or temperature; and other factors.

Toxic conditions can be detected and remedied immediately in individually controlled artificial niches. Thus, application of embodiments of the invention can facilitate producing healthy cells with increased product yield and/or quality.

Furthermore, in traditional cell culture, the medium and the cells are often stirred to reduce their local concentration in the culture chamber. Stirring can generate harmful levels of shear for cells. In a controlled artificial niche, culture medium can be provided to the cell and the concentration gradients can be controlled without stirring the medium or the cells, thus avoiding the harmful shear forces resulting from stirring.

Furthermore, basal conditions in niches (i.e. the conditions of the cells in the absence of toxic conditions) can be controlled to achieve better product yield than in traditional bulk cultures.

One or more niches in a bulk culture device can be individually controlled and monitored. Cells cultured in the controlled niches can be observed constantly at high magnification and/or with biosensors. In such a case, these cells can be used to monitor the conditions of the bulk culture as a whole.

Further, optimized cell-scale niches can be arrayed in small particles for the culture of niche-dependent cells in standard stirred-tank bioreactors.

(vii) "Organism on a Chip"

Embodiments of the invention can be used to produce systems of mutually-supporting cell types. Assemblies of individually controlled artificial niches of different cell types are connected in a subnetwork that performs the function of an organ, and these subnetworks are connected in a larger network that performs the function of organ systems of an organism. For example, a single device may control niches of the different cell types found in kidney, and also niches for the different cell types found in liver, and all of the organs of the body.

Niches for cells from different tissues of an organism are in chemical communication with each other through a circulatory system network that mimics that of the organism. The system of niches reproduces the functions and physiology of an organism.

Figure 14A:
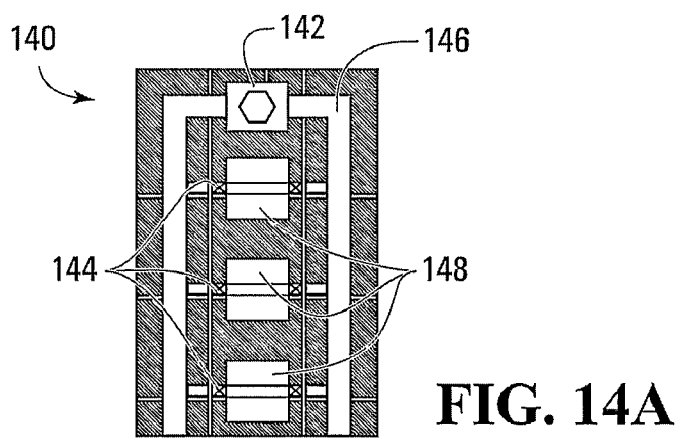
FIG. 14A is a schematic top plan view of a cell culturing apparatus, exemplary of an embodiment of the invention.
Figure 14B:
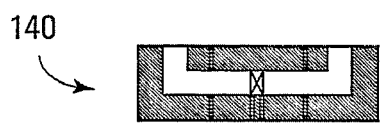
FIG. 14B is a schematic front plan view of the cell culturing apparatus of FIG. 14A.

An exemplary device 140 is shown in FIGS. 14A and 14B, which has a simple network. As can be understood, the network could have a different topology as shown in FIGS. 14A and 14B. Device 140 includes a pump 142, valves 144 and fluid communication channels 146 for maintaining chemical communication among niche chambers 148. The digestive system and circulatory system of natural organism can be reproduced within device 140 so that cells cultured in device 140 can be fed with more complex culture substances such as food.

(viii) Niche-Optimized Wound Dressings

One or more artificial niches may interface directly with a natural layer of cells or natural tissues. For example, a layer of niches may be formed in a cell culturing device with the top of each niche left open until the layer of niches is put adjacent and in contact with a treatment site on a patient, at which time a natural tissue in the patient forms the top boundary of the niches in the layer.

As a specific example, for the regrowth of gums on teeth, the bare dentin or enamel can be covered with a niche wound dressing that exposes cells in the niches to the dentin so that they can attach, and also exposes cells on the edge of the wound dressing that is facing the existing gums to cells in the gums that can be exposed by removing the surface layers.

Figure 15:
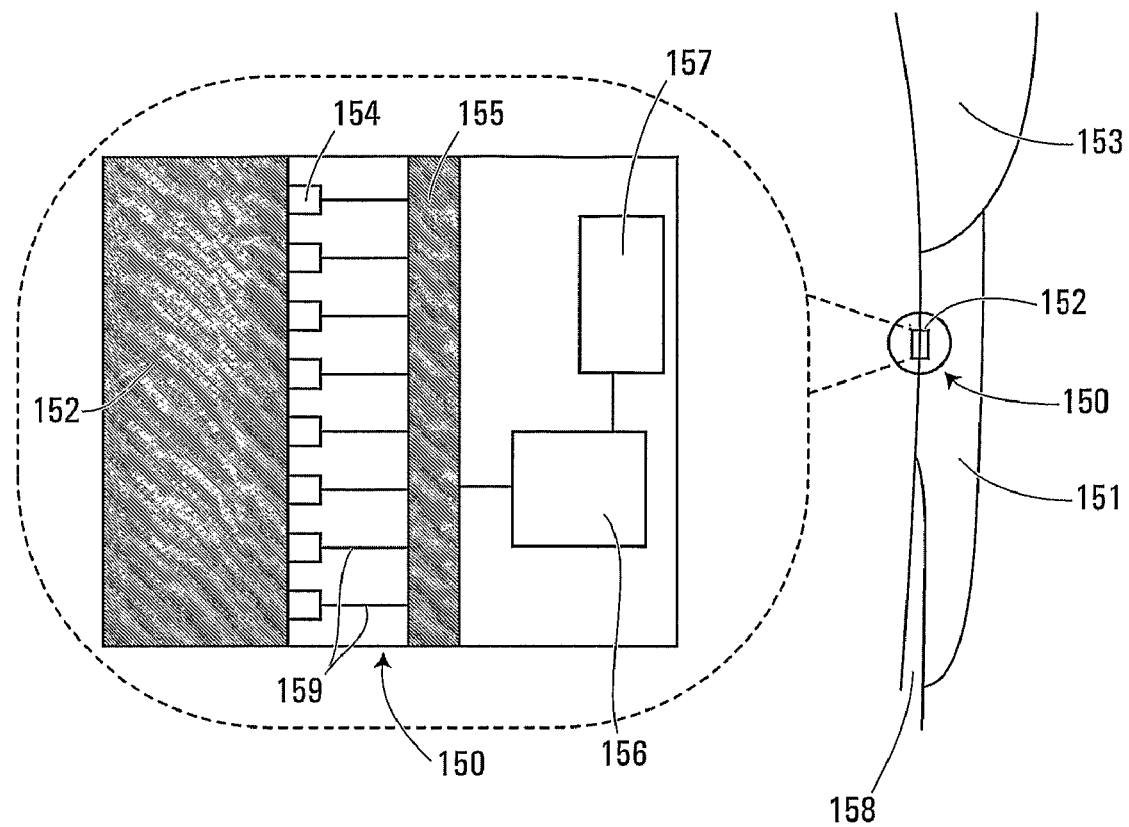
FIG. 15 is a schematic diagram illustrating the application of a wound dressing, exemplary of an embodiment of the invention.

While the cells in the niches are attaching to the dentin and to other cells, they are being supplied with nutrients, mechanical support, gradients of growth factors, and other niche components on all sides bounded by the niche chamber. The niche chambers may be connected with canals and valves to allow cells to migrate from the existing tissue into the niches. This specific example is illustrated in FIG. 15, which shows a wound dressing 150 designed to support tissue regeneration. A tooth 151 is rooted on its gum 153. Gum 153 has receded exposing dentin 152. Dressing 150 defines a number of niche chambers 154 with one side open. The open side is affixed flush against dentin 152 so that cells (not shown) in niche chambers 154 can attach to dentin 152 over a prolonged period. The cells are fed nutrients through channels 159 from a media reservoir 155 pressurized by microfluidic pumps 156 using energy from power supply 157. The dressing is made of a flexible material such as PDMS so that it can conform to the surface of dentin 152, gum 153, and enamel 158.

(ix) Variable Shape

The shape of a niche chamber, and hence the shape of an artificial niche, may undergo controlled change during culturing to accommodate changing morphology of the cell, for example, during growth or differentiation.

Figure 16A:
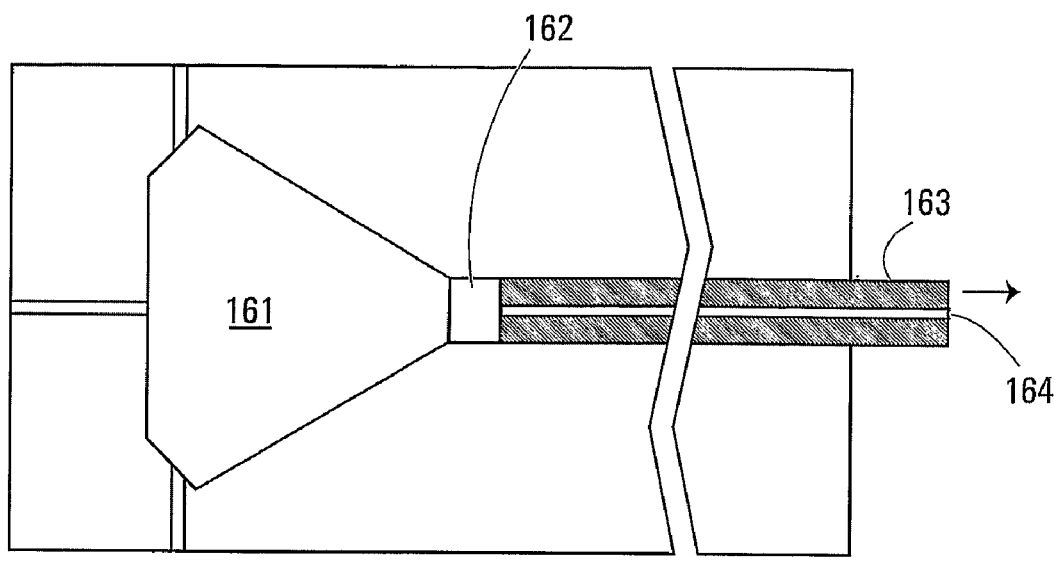
FIG. 16A is a schematic top view of a cell culturing apparatus, exemplary of an embodiment of the invention.
Figure 16B:
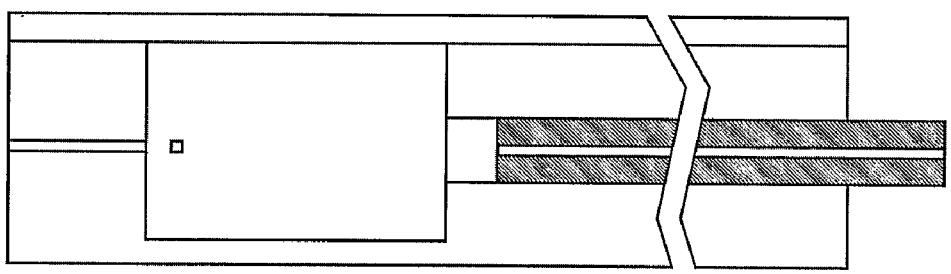
FIG. 16B is a schematic front view of the apparatus of FIG. 16A.

FIGS. 16A and 16B show an example of a niche chamber 161 which changes its shape to accommodate the growing axon of a neural precursor cell as it is differentiated. Niche chamber 161 is connected to a tube 162 containing a plunger 163 with a lumen 164.

In operation, niche chamber 161 is seeded with a rounded-up neuronal precursor. A molecule that attracts the growth cone of the axon is fed through lumen 164 of plunger 163 into chamber 161. As the axon of the neuron moves towards the plunger tip the tip is withdrawn into tube 162. Tube 162 can be meters long if necessary. Niches of cells such as Schwann cells can line tube 162 to myelinate the axon. When the axon has grown, the top of niche chamber 161 can be removed so the axon can be harvested. Molecules released from patch clamps in the corners of the niche chamber simulate the presence of synapses to stimulate the neuron.

An artificial niche can also undergo controlled expansion radially. This can be accomplished for example by surrounding the niche with gels or solids that can be compressed or broken down to make way for growing and dividing cells.

For example, in a culturing device made to accommodate a growing follicle destined to become an ovum, the size of the niche chamber must increase from about 10 microns in diameter to over 100 microns in diameter to accommodate the growing follicle alone, and must be larger if it is also to include the granulose cells that surround the follicle, and finally the fluid-filled antrum that borders the ovum preceding ovulation.

Figure 17A:
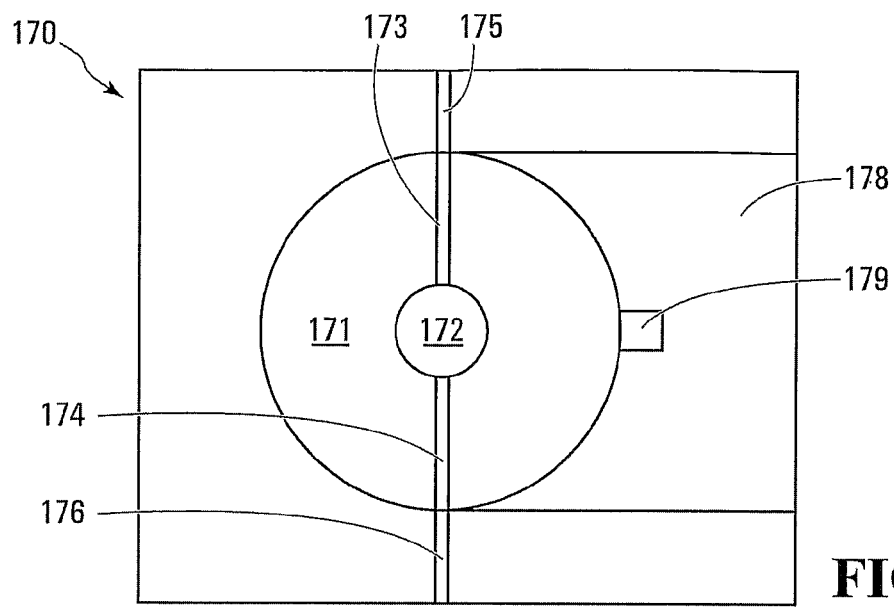
FIG. 17A is a schematic top view of a cell culturing apparatus, exemplary of an embodiment of the invention.
Figure 17B:
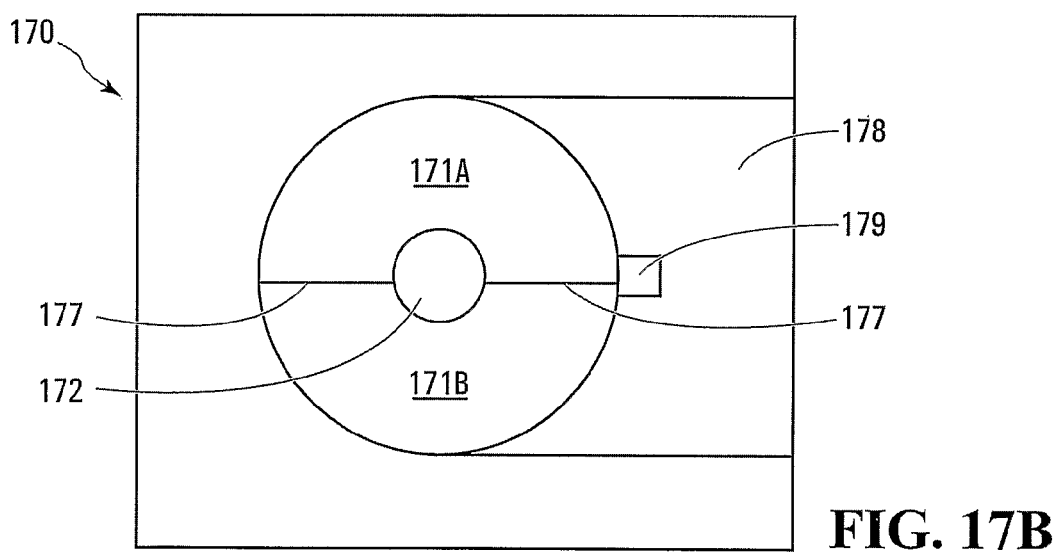
FIG. 17B is a schematic front view of the apparatus of FIG. 17A.
Figure 18:
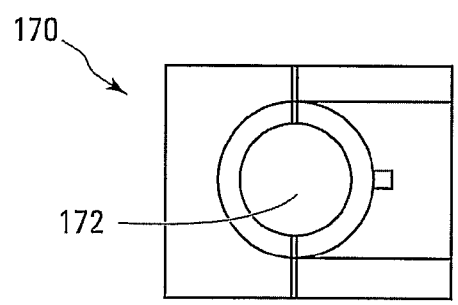
FIG. 18 is a schematic top view of the apparatus of FIG. 17A in operation.

An exemplary cell culturing device having an expandable niche chamber is illustrated in FIGS. 17A, 17B and 18. The cell culturing device 170 has an enclosure for receiving a gel 172, which in turn defines a niche chamber 172. Gel 171 comprises two half-spheres 171A and 171B pressed towards each other along the borderline 177. Gel 171 may be loaded into device 170 through channel 178 by a plunger (not shown). Channels 173 and 174, which pass through gel 171 and can be connected with channels 175 and 176 on device 170, provide passageways for feeding and draining liquids to and from niche chamber 172. A tab 179 can be provided to abut gel 171 so as to keep channels 173 to 176 properly aligned.

In operation, a primary follicle is loaded in niche chamber 172 with a single layer of granulose cells by micropipette and micropositioner outside device 170. Gel 171 can be made of biomolecules in patterns that simulate the stromal cells to which the granulose cells are naturally exposed to in the ovary. Additional channels (not shown) that open on the outside of the gel can supplement this function by diffusing solutions throughout the gel. The two gel halves 171A and 171B are brought together to form gel 171 enclosing the loaded follicle and gel 171 is inserted into device 170 with a plunger through channel 178. The culturing fluid can be fed to the niche in a manner to simulate the polarizing gradient of nutrients and growth factors to which a natural growing follicle is exposed in the ovary due to its position relative to the blood supply in the medulla. As the follicle and granulose cells grow they push against gel 171 and enlarge niche chamber 180, as illustrated in FIG. 18, mimicking the expansion occurring in natural ovary due to cells pushing against the stromal cells in the ovary. To make room for the expanding cell(s), gel 171 may be made of compressible material so that it can be compressed under pressure from the cells. Alternatively, gel 171 may be made of digestible or consumable material so that it can be partially digested or consumed. For example, alginate or collagen gels may be digested by alginases or collaginases, respectively. Breakdown products can be flushed out by perfusion.

(x) Lineage Informatics Study

Figure 19A:
FIGS. 19A and 19B are photographs of an actual cell culturing device.
Figure 19B:
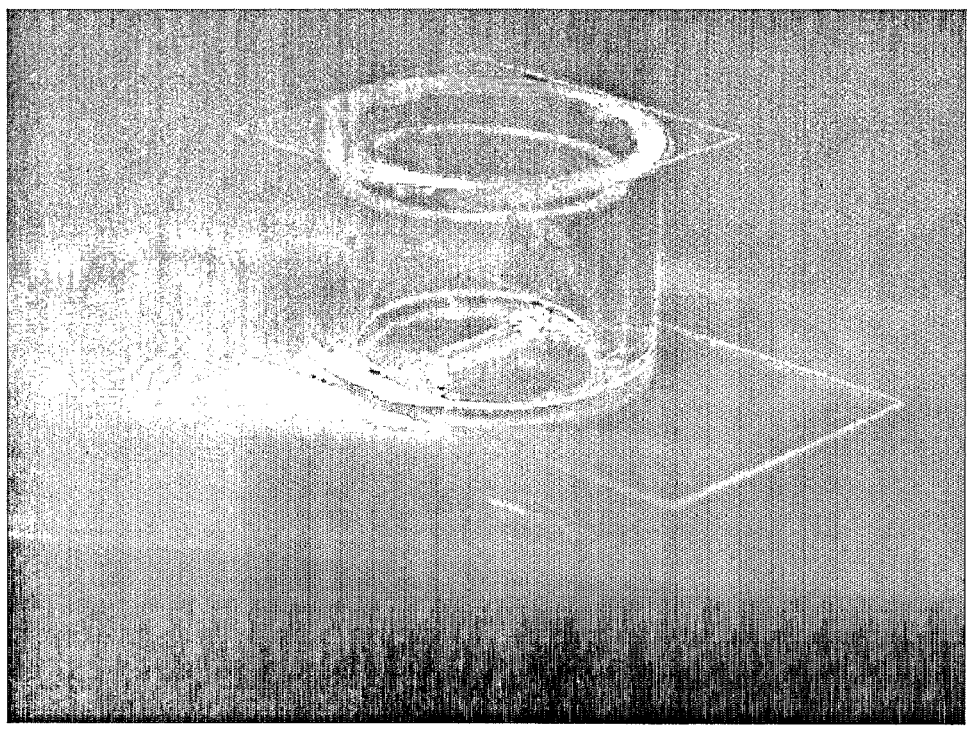

A lineage informatics study was conducted using a confined-cell culture device shown in FIGS. 19A and 19B.

The culture chamber in this device was formed using a 22×50 mm cover slip (as the bottom plate) and a 1.3×8×1 mm microscope slide (as the top plate). The ends of the microscope slide were glued to the cover slip as they were held together using a small clamp. The glue used was medical grade Type-A silicone adhesive (Dow-Corning™). The glue was allowed to cure for more than 72 hours before exposure to cells. After the glue was dried, the clamp was removed and a glass tube was glued around the chamber to form a well which would serve as a media reservoir, as shown in FIG. 19A. A snug-fitting lid with a cover slip top was provided for covering the well, as shown in FIG. 19B. The lid was useful for preventing contamination while minimizing light scatter during imaging.

The cells were prepared and cultured as follows.

Adult male CD1 mice (25-30 g; Charles River, Quebec, Canada) were killed by cervical dislocation and neural'stem cells were isolated as described in V. Tropepe et al., "Transforming growth factor-alpha null and senescent mice show decreased neural progenitor cell proliferation in the forebrain subependyma", Journal of Neuroscience, (1997), vol. 17, pp. 7850-7859 ("Tropepe 97"), which is incorporated herein by reference. Briefly, brains were removed and placed in oxygenized artificial cerebrospinal fluid containing 1.3 $MgCl_2$, 26 $NaHCO_3$, 10 D-glucose, 124 NaCl, 5 KCl, and 2 $CaCl_2$ (all in mM). The lateral ventricle subependyma was dissected and placed in enzyme solution (1.33 mg/ml trypsin (Sigma), 0.67 mg/ml hyaluronidase (Sigma), and 0.2 mg/ml kynurenic acid (Sigma) for 30 min. at 37° C. Tissue was transferred to serum-free medium containing 0.7 mg/ml trypsin inhibitor (Roche™) and centrifuged at 1500 rpm for 5 min. The supernatant was removed and replaced with complete media (CM) consisting of serum free media, 20 ng/ml epidermal growth factor (EGF, mouse submaxillary; Sigma™), 10 ng/ml fibroblast growth factor (FGF2, human recombinant; Sigma), and 2 ug/ml heparin (Sigma). The pellet was triturated with a sterile fire-polished Pasteur pipet and centrifuged again at 1500 rpm for 5 min. The pellet was then re-suspended in CM and cells were cultured at a clonal density of less than 20 cells/ul.

After generation of primary neurospheres, cultures were bulk passaged every 5-7 days as described in V. Tropepe et al., "Distinct neural stem cells proliferate in response to EGF and FGF in the developing mouse telencephalon", Developmental Biology, (1999), vol. 208, pp. 166-88 ("Tropepe 99"), which is incorporated herein by reference. Briefly, neurospheres were collected, centrifuged at 1500 rpm for 5 minutes, re-suspended in CM, triturated to a single cell suspension using a fire-polished pipette and plated in CM. Cells were replated at clonal density in tissue culture flasks (Nunc™, Naperville, Ill.).

Polystyrene microspheres with a mean diameter of 5.8 μm (Polysciences™) were rinsed three times in NanoPure™ water and then air dried. The microspheres were sterilized under a UV lamp and then re-suspended in CM. The Neurospheres were taken up in a 10 μL siliconized pipette tip and triturated 5 to 15 times against a sterile cover slip glass until turbid. The cell suspension was then filtered through a sterile 40 μm nylon sieve (Becton Dickinson™). The cell density of the filtrate was adjusted to $10^6$ cells/mL. The microspheres were added to a density of $3 \times 10^6$ microspheres/mL. The top plate was lifted with rubberized tweezers and 2 uL of cell/microsphere suspension was placed at the chamber edge to allow the suspension to be drawn in to the gap by capillary action. The top plate was then lowered gently over a period of a few seconds. Excess cell suspension expelled when the top plate was lowered was pipetted away from the opening of the gap between the top and bottom plates. The well was then filled with 1 mL of fresh CM and the cells were allowed to grow.

Washes and incubations following fixation were done in a shaker at 120 rpm to encourage transport of reagents into the confined culture space in the culture chamber. Cells were washed, fixed with 4% paraformaldehyde for 15 minutes, permeabilized for 5 minutes with 0.3% Triton X-100, and blocked for 1 hour in 10% goat serum. Cells were incubated for 1 hour with rabbit anti-GFAP (Chemicon™), mouse anti-β-tubulin III IgG (Sigma), mouse anti-O4 IgM (Chemicon™), mouse anti-nestin IgG, or mouse anti-S100 IgG. Following staining with primary antibodies cells were washed for 2 hours and then incubated for 30 minutes with appropriate secondary antibodies: AMCA-conjugated goat anti-rabbit IgG, fluorescein-conjugated goat anti-mouse IgM, and rhodamine-conjugated goat anti-mouse IgG (Jackson Immunoresearch™). Cells were stained with Rhodamine-conjugated phalloidin (Molecular Probes™) for 30 minutes at room temperature.

Cultured cells were imaged on an inverted microscope (Zeiss, Axiovert 200™) using DIC optics. The cell culturing chamber was maintained at 37° C. in a 5% $CO_2$ humidified air atmosphere. Samples were illuminated every three minutes during image acquisition and kept in the dark otherwise. Images were captured with a digital camera (Sony™, Japan). Initially, cells were imaged at low magnification (5×) until a single cell was observed to divide, after which the developing colony was imaged at 40× magnification.

Lineage informatics information was obtained as follows. A number of image frames were taken over a period of time, such as about 109 hours. Each cell in each frame of the image sequence is scored for position, and microenvironmental, behavioral, and morphological variables specific to the objectives of the experiment. The derived values such as speed and proximity to other cells or the colony were calculated using a computer and specially developed software. The merged data set could be queried and analyzed in the context of the lineage tree using a variety of 2D and 3D views, pattern searches, and cluster analyses.

Figure 20:
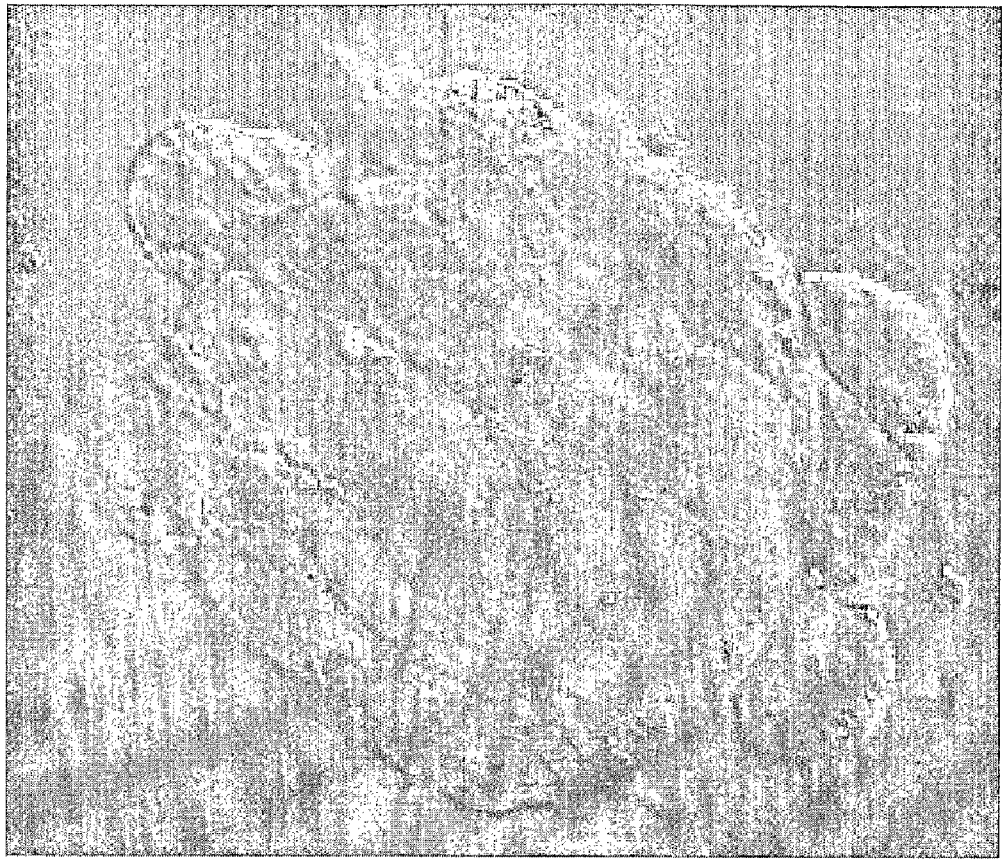
FIG. 20 is a DIC image of cells cultured in the device of FIG. 19.

It was found that DIC or confocal imaging did not permit individual cells in neurospheres to be distinguished consistently beyond approximately 15 μm beneath the surface. To overcome this limitation, dissociated UNCs were confined between parallel glass plates separated by 5.8 μm polystyrene microspheres. The growing colony can be referred to as "neurodisk" because cells were geometrically confined to a single layer within the chamber and generally form roughly circular colonies. This confined-geometry culture system allowed long-term high resolution viewing of all cells in a developing colony. The complete development of a clonally-derived colony was monitored with images taken every 3 minutes. FIG. 20 shows an image of a colony of 26 cells which developed from a single cell over five days. It was observed that during the culture there were three cell deaths and one cell migrated out of the field of view. Individual cells did not migrate, rotate, or spread significantly when not in contact with another cell. Conversely, cells in contact with other cells migrated constantly and extended themselves against each other. This suggests that the confining surfaces do not support sufficient cell attachment for migration or spreading. Thus this culture system is effectively non-adherent. Movements of cells on the surface of the neurospheres were also observed using time lapse imaging technique.

Because cells were confined to grow in a space only 5.8 μm thick, intracellular details were visible. Vesicles and vesicle transport were also visible and greatly facilitated cell tracking. Cell blebbing (i.e. the formation of small membrane bubbles along the border of the cell) was sometimes visible on the periphery of some disks.

To track the development of a single-cell-derived disk, DIC images were collected over 109 hours. The images were analyzed to obtain lineage relationships in cell culture. For example, a cell's position, morphology, and behavior in each image in the sequence were tracked. The complete image sequence record allowed the reconstruction of the lineage history of the colony. From the manually entered position and phenotype data, derived characteristics including position within the cell group, nearest neighbor history, speed, and cell area, were calculated.

In the confined culture geometry, mitotic spindle axes were always perpendicular to the viewing axis facilitating the study of division symmetry. Parameters that can be measured using this culturing device include relative sizes and shapes of the daughters, location of mitoses relative to the cell mass, orientation of the spindle axis, chromosomal orientation, and apportioning of the cytoplasm and its components between sisters. Each of these variables can be included in the lineage analysis for sister cell fate comparisons.

As now can be appreciated, embodiments of the invention can have certain advantages over conventional culturing devices and processes.

For instance, it is possible to culture a single cell with precisely controlled properties in an artificial niche provided by an embodiment of the invention, for example, by depositing particular desirable molecules or cells adjacent a target cell and/or by removing a particular neighbouring cell from the artificial niche. It is also possible to control the gradient concentration in the culture media such as nutrients and oxygen gas, which in turn can be used to encourage orientation and location of certain cells (for example cells may move in a desired direction to seek source materials). Thus, the niches provided by the apparatus can mirror a biological niche.

It is also possible in various embodiments to monitor the niche and cell growth at a single cell level during a prolonged period, for example, to obtain and record a complete growth history for a single cell. It is therefore possible to acquire a precise knowledge of the biological properties of a grown cell, including its precise phenotype. Further, confining cells between barriers can facilitate direct observation of cell growth and subcellular detail in live cells with imaging techniques such as standard bright field imaging or fluorescent imaging without the use of a confocal microscope or a laser imaging device. As can be understood, when cells are confined within the proximity of the in-focus-plane of an object lens, the image quality can significantly improve as compared to images of cells that can move away from the in-focus-plane. Experiments have shown that cells cultured within a one-dimensional confine on the order of 5 microns can be imaged with significantly improved subcellular resolution. Further, high resolution images can be obtained without exposing cultured cells to high intensity light which would be required if a conventional high resolution imaging technique such as confocal imaging technique were used. As a result, these cells were confined and imaged for many days (such as from about one day to many weeks) without apparent ill effect on the cells (including loss of viability or material change in the proliferation rate). Therefore, it is possible to perform long term imaging of the confined cells with high resolution techniques such as differential interference contrast (DIC). While laser scanning confocal microscopy can provide comparable resolution of fluorescently tagged cells, as discussed earlier, laser-induced phototoxicity severely limits the duration of a live-cell imaging using this technique. Thus, using embodiments described above, images of a sample of cultured cells can be taken over a period of time that is longer than what is possible using a confocal microscope to image the same sample. Further, the above-mentioned non-confocal imaging techniques can be performed using equipments less expensive than those that are typically used in confocal imaging techniques or other conventional high resolution techniques such as multiphoton imaging and Nipkow disk imaging techniques.

When an assembly of cells are confined to a single layer, it is easy to remove a specific cell, or a group of cells, from the assembly. Thus, it is possible to control the resulting cultured cell population, such as to ensure that there is no cell in the resulting population that has a certain undesirable phenotype.

Other features, benefits and advantages of the present invention not expressly mentioned above can be understood from this description and the accompanying drawings by those skilled in the art.

As can be understood by a person skilled in the art, many modifications to the exemplary embodiments of the invention described herein are possible.

For example, spacers 34 may be replaced by other spacing members. Non-spherical spacers may be used. Barrier plates may also be separated by a grided planar spacer sandwiched between them, thus defining a plurality of niche chambers.

It is also possible to place an array of niche chambers 30 within chamber 26.

It is not necessary for the bottom barrier plate to be the same base plate 22 that forms container 25. Instead, the bottom barrier plate and the base plate can be two separate plates, in which case the bottom barrier plate may be detachable from container 25 and both barrier plates may be removable from chamber 26.

As alluded to earlier, additional barrier members such as a dam may be removably or fixedly mounted in the container adjacent the cover plate so as to block flow of media liquid, either partially or completely, thus controlling the gradient of the medium in the culture chamber, or creating a unidirectional gradient in the chamber.

It is also possible to place an array of culture niche chambers 30 in one medium container 25.

Additionally, while the construction and operation of apparatus 40 is described above with reference to culturing spermatogonia cells, it will be readily apparent to persons skilled in the art that apparatus 40 can be modified to create an appropriate or desirable microenviromnent for a different cell type.

The possible sizes of niche chamber 30 or 48 may range between 100 nanometers to 10 cm.

The culture chambers or niche chambers may be pressurized in certain applications.

The inner surfaces of niche chambers 30 or 48 may be dynamically controlled during cell culture, for example by using surface coatings that become hydrophobic or hydrophilic by the application of a voltage potential. The surface shapes may be changed during the growth or differentiation of cells, for example by using inflatable bladders or moving walls with actuators such as piezoelectric crystals.

Other characteristics that can be monitored or controlled in a niche before or during culture include but are not limited to: freedom with which molecules can diffuse to and away from the cell; freedom with which liquid can flow; concentrations of gases, liquid molecules, biological or other polymers, signalling molecules, and other molecules; strengths of concentration gradients of these molecules; presence of such molecules attached to surfaces, to other molecules, and other cells; pH; temperature; topology, hardness, selective permeability, and chemical makeup of surfaces near or touching the cell; amount of dynamic movement of objects near the cell; density of cells surrounding a niche; and types of cells near a given cell.

Cells may be loaded or unloaded from culture chambers or niche chambers by centrifuging, moving with magnetic particles, or attracting with a chemoattractant.

Temporary dividers may be included to prevent cells from accessing certain regions of the culture space until the dividers are moved or destroyed, for example to allow a cell type to grow or extend processes, or to prevent two cells from touching until the divider is removed. The dividers may be moved or destroyed by hydraulic, mechanical, electrical, chemical, or other means.

Solid materials, for example specifically coated microspheres used as spacers or for other purposes, may be introduced to the culture spaces during culturing using microfluidic channels, micropipette deposition, optical tweezers, or other means.

The culture chambers or niche chambers may be mutagenic, for example by containing sources of radiation or exposing them to short wavelength light. This may be advantageous for conducting forced evolution experiments.

The embodiments of the invention may be utilized to culture any type of cells, including prokaryotic and eukaryotic cells, mammalian cells such as stem, progenitor, terminally differentiated, transformed, normal, or embryonic cells.

The embodiments of the invention may be used to provide validation that a cultured cell is appropriate for medical use by logging its history (behavioural, morphological, and environmental).

Electrodes may be provided on apparatus 10 and 40 to detect electrical responses of cells such as neurons in response to the presence of molecules or other stimuli of interest. For example, electrical or fluorescent responses produced by the cells in the niches may be used to detect neurotoxins or other bioactive agents.

Embodiments of the invention may be implanted into an organism. Possible uses of such implanted devices include the secretion of beneficial biomolecules in response to the host organism's environment, or filtering of blood, lymph, or other fluids.

Cells may be cultured in accordance with or using embodiments of the invention for use as an artificial tissue, organ, cell transplant, or ill vitro fertilization.

As will be understood, the above examples merely demonstrate the possible applications and variations of embodiments of the invention. The invention, rather, is intended to encompass all such modification within its scope, as defined by the claims.

What is claimed is:

1. A method of cell culture comprising:
confining a cell between first and second barriers, said barriers spaced at a distance to contact said cell and prevent said cell from traveling toward or away from each of said first and second barriers;
placing one or more spacers between said first and second barriers to prevent said first and second barriers overcompressing said cell; and
providing to said cell a culture substance,
wherein said first barrier is urged toward abutment with said second barrier and wherein said confining and said placing comprise at least partially separating said first and second barriers and introducing said cell and said one or more spacers between said first and second barriers, wherein said one or more spacers are rigid spheres.

2. The method of claim 1 wherein said providing comprises establishing a concentration gradient of said culture substance within said space.

3. The method of claim 1 further comprising manually positioning another cell adjacent said cell.

4. The method of claim 1 wherein said first and second barriers comprise first and second plates.

5. The method of claim 1 wherein a monolayer of cells is cultured between said barriers.

6. The method of claim 5, further comprising removing a cell from said monolayer of cells when said cell to be removed is observed to meet one or more criteria.

7. The method of claim 6, wherein said one or more criteria are related to one or more of karyotype, morphology, and size.

8. The method of claim 1 further comprising:
limiting the number of cells surrounding said cell to permit control of a microenvironment surrounding said cell.

9. The method of claim 1 wherein said introducing comprises introducing a suspension of said cell and said one or more spacers between said first and second barriers.

10. The method of claim 1 further comprising fixing ends of said second barrier to said first barrier with an elastic fixative, said elastic fixative urging said first barrier toward abutment with said second barrier.

11. The method of claim 1 wherein said cell is confined between a surface of said first barrier and a surface of said second barrier, each surface selected to limit adhesion of said cell to said each surface.

12. The method of claim 1 wherein said providing comprises flowing said culture substance to said cell at a controlled rate.

13. The method of claim 4, wherein said plates are optically transparent.

14. The method of claim 1 wherein said providing comprises allowing said culture substance to permeate through one or both of said first and second barriers to between said first and second barriers.

15. The method of claim 1 further comprising sensing, with a sensor disposed adjacent a space between said first and second barriers, one or more of molecular concentration, temperature, osmolarity, pH, and shear force.

16. The method of claim 11 wherein said surface of said first barrier comprises molecules of a first type and said surface of said second barrier comprises molecules of a second type.

17. A combination of cell culture device and cell culture comprising:
first and second barriers and one or more spacers therebetween defining a desired cell culture space, said barriers contacting cells or bodies of cells constrained in said culture space, wherein the spacers are sufficiently rigid to resist movement of said first and second barriers and are sized to approximate the size of said cells or bodies of cells so as to prevent said first and second barriers from overly compressing said cells or bodies of cells; and
means for providing to said culture space a culture substance,
wherein said barriers comprise a microscope cover slip, and at least a portion of one of said barriers is transparent.

18. The combination of claim 17 wherein said means for providing to said space a culture substance comprises one or more fluid passageways allowing fluid communication to and from said space.

19. The combination of claim 18, wherein said one or more fluid passageways comprise one or more microfluidic channels each terminating adjacent said space.

20. The combination of claim 17 further comprising means for regulating fluid flow to or from said space.

21. The combination of claim 17 wherein at least one of said first and second barriers is permeable to nutrients and gases.

22. The combination of claim 17 further comprising means for monitoring said cells or bodies of cells constrained in said space.

23. The combination of claim 22 wherein said means for monitoring comprises a sensor.

24. The combination of claim 23 wherein said sensor is a sensor for sensing one or more of molecular concentration, temperature, osmolarity, pH, and shear force.

25. The combination of claim 23 further comprising one or more transparent electrodes for connecting said sensor to a control system.

26. The combination of claim 17, wherein said portion of said barrier is made of a contact lens material.

27. The combination of claim 17 wherein at least one of said barriers is moveable for adjusting the size of said space.

28. The combination of claim 27, further comprising an actuator for moving said at least one of said barriers.

29. The combination of claim 28, wherein said actuator comprises one or more of an inflatable bladder, a screw, a lever, a clamp, a micrometer, and a piezoelectric crystal.

30. The combination of claim 17 wherein said one or more spacers are removable from said first or second barrier.

31. The combination of claim 17 wherein said one or more spacers are molded on said first or second barrier.

32. The combination of claim 17 further comprising a divider for dividing said space into a plurality of regions and for preventing said cells or bodies of cells from moving between said regions.

33. The combination of claim 32, wherein said divider is removable.

34. The combination of claim 17 wherein the surfaces of said barriers comprise different types of molecules.

35. The combination of claim 17 comprising a permeable membrane positioned to cover an opening adjacent said space for preventing said cells or bodies of cells from leaving said space through said opening.

36. The combination of claim 17 wherein said barriers define a plurality of spaces for confining a plurality of cells therebetween.

37. The combination of claim 17 which is included in a cartridge.

38. The combination of claim 17 further comprising a fluid culture medium which immerses said cells or bodies of cells.

39. The combination of claim 38, comprising a septum allowing access to said space with a syringe or a pipette.

40. The combination of claim 17 further comprising a capillary conduit for transporting a cell-containing fluid to or from said space.

41. A combination of a cell culturing device and a cell culture, comprising:
   a container defining a chamber for receiving a fluid culture medium;
   at least two barriers defining a space in said chamber;
   an assembly of two or more cells constrained in said space so as to keep said assembly therein and in continuous contact with each of said at least two barriers during culturing; and
   means for providing to said space a culture substance, wherein one of said barriers is a microscope cover slip, and at least a portion of one of said barriers is transparent.

42. The combination of claim 41 wherein said space is sufficiently small to permit control of a microenvironment surrounding an individual cell in culture.

43. The combination of claim 41 wherein said assembly comprises a monolayer of cells.

44. The combination of claim 41 wherein said means for providing to said space a culture substance comprises one or more fluid passageways allowing fluid communication to and from said space.

45. The combination of claim 44, wherein said one or more fluid passageways comprise one or more microfluidic channels terminating adjacent said space.

46. The combination of claim 41 further comprising means for regulating fluid flow to or from said space.

47. The combination of claim 41 wherein at least one of said at least two barriers is permeable to nutrients and gases.

48. The combination of claim 41 further comprising means for monitoring said cell constrained in said space.

49. The combination of claim 48 wherein said means for monitoring comprises a sensor disposed in said chamber.

50. The combination of claim 49 wherein said sensor is a sensor for sensing one or more of molecular concentration, temperature, osmolarity, pH, and shear force.

51. The combination of claim 49 further comprising one or more transparent electrodes for connecting said sensor to a control system.

52. The combination of claim 41, wherein said portion of said barrier is made of a contact lens material.

53. The combination of claim 41 wherein at least one of said bathers is moveable for adjusting the size of said space.

54. The combination of claim 53, further comprising an actuator for moving said at least one of said barriers.

55. The combination of claim 54, wherein said actuator comprises one or more of an inflatable bladder, a screw, a lever, a clamp, a micrometer, and a piezoelectric crystal.

56. The combination of claim 41 further comprising one or more spacers placed between said bathers for preventing said barriers over-compressing said cell.

57. The combination of claim 56, wherein said one or more spacers are molded on one or more of said bathers.

58. The combination of claim 41 further comprising a divider for dividing said chamber into a plurality of regions and for preventing said cell from moving between said regions.

59. The combination of claim 58, wherein said divider is removable from said container.

60. The combination of claim 41 wherein the surfaces of said bathers comprise different types of molecules.

61. The combination of claim 41 comprising a permeable membrane positioned to cover an opening adjacent said space for preventing a cell from leaving said space through said opening.

62. The combination of claim 41 wherein said barriers defining a plurality of spaces for confining a plurality of assembly of cells therebetween.

63. The combination of claim 41 which is included in a cartridge.

64. The combination of claim 41 further comprising said fluid culture medium which is contained in said chamber and immerses said assembly of cells.

65. The combination of claim 64, wherein at least one wall of said container has a septum allowing access to said space with a syringe or a pipette.

66. The combination of claim 41 further comprising a capillary conduit for transporting a fluid to or from said space.

67. An apparatus for culturing cells in a controlled environment comprising:
   i) first and second barriers and one or more spacers therebetween defining a desired confined space, wherein the distance between the barriers approximates the size of cells or bodies of cells to be cultured therein such that both the first and second barriers contact said cells or bodies of cells to impede their movement, wherein said spacers are sufficiently rigid to resist movement of said first and second barriers and prevent said first and second barriers from overly compressing said cells or bodies of cells.
   ii) the inner surface of one or both of said first and second barriers having one or more characteristics or properties selected to mimic the characteristics of the biological environment of said cells;
   iii) means for providing a culture substance to said space, wherein one of said barriers is a microscope cover slip, and at least a portion of one of said barriers is transparent.

68. The apparatus of claim 67 wherein said barriers comprise two opposing glass plates.

69. The apparatus of claim 67 wherein said space is so sized as to confine a single cell.

70. The apparatus of claim 67 wherein said space limits cells cultured therein to a monolayer.

71. The apparatus of claim 67 wherein said means for providing comprises one or more fluid passageways allowing fluid communication to and from said space.

72. The apparatus of claim 71 wherein said one or more fluid passageways comprise one or more microfluidic channels terminating adjacent said space.

73. The apparatus of claim 67 further comprising means for regulating fluid flow to or from said space.

74. The apparatus of claim 67 wherein at least one of said barriers is permeable to nutrients and gases.

75. The apparatus of claim 67 further comprising means for monitoring a cell constrained in said space.

76. The apparatus of claim 75 wherein said means for monitoring comprises a sensor.

77. The apparatus of claim 76 wherein said sensor is a sensor for sensing one or more of molecular concentration, temperature, osmolarity, pH, and shear force.

78. The apparatus of claim 76 further comprising one or more transparent electrodes for connecting said sensor to a control system.

79. The apparatus of claim 67, wherein said portion of said barrier is made of a contact lens material.

80. The apparatus of claim 67 wherein at least one of said barriers is moveable for adjusting the size of said space.

81. The apparatus of claim 80, further comprising an actuator for moving said at least one of said barriers.

82. The apparatus of claim 81, wherein said actuator comprises one or more of an inflatable bladder, a screw, a lever, a clamp, a micrometer, and a piezoelectric crystal.

83. The apparatus of claim 67 wherein said one or more spacers are removable from said first or second barrier.

84. The apparatus of claim 67 wherein said one or more spacers are molded on said first or second barrier.

85. The apparatus of claim 67 further comprising a divider for dividing said space into a plurality of regions and for preventing said cells or bodies of cells from moving between said regions.

86. The apparatus of claim 84, wherein said divider is removable.

87. The apparatus of claim 67 wherein the surfaces of said barriers comprise different types of molecules.

88. The apparatus of claim 67 comprising a permeable membrane positioned to cover an opening adjacent said space for preventing a cell from leaving said space through said opening.

89. The apparatus of claim 67 wherein said barriers defining a plurality of spaces for confining a plurality of cells therebetween.

90. The apparatus of claim 67 which is included in a cartridge.

91. The apparatus of claim 67 further comprising a fluid culture medium in said space.

92. The apparatus of claim 91, comprising a septum allowing access to said space with a syringe or a pipette.

93. The apparatus of claim 67 further comprising a capillary conduit for transporting a fluid to or from said space.

94. A method of cell culturing, comprising:
culturing one or more cells while restricting movement of said one or more cells such that each one of said one or more cells is in continuous contact with two opposing barrier surfaces and is mobile between said barrier surfaces, wherein said barrier surfaces are substantially parallel with each other; and
during said culturing, obtaining one or more images of said one or more cells.

95. The method of claim 94 wherein said barrier surfaces are substantially planar.

96. The method of claim 94, wherein said one or more images are obtained using a non-confocal imaging device.

97. The method of claim 94, wherein said one or more images are obtained using a bright field imaging device or a fluorescent imaging device.

98. The method of claim 97, wherein said one or more images are obtained using a differential interference contrast (DIC) imaging device.

99. The method of claim 94 wherein said one or more images comprise a plurality of images taken over a period of time longer than about one day.

100. The method of claim 94 wherein said one or more images comprise a plurality of images taken over a period of time which is not limited by significant or substantial phototoxic effects to impose a constraint for gathering information on behavior histories of a cell or cells.

* * * * *

UNITED STATES PATENT AND TRADEMARK OFFICE
CERTIFICATE OF CORRECTION

PATENT NO. : 7,919,319 B2  
APPLICATION NO. : 10/582975  
DATED : April 5, 2011  
INVENTOR(S) : Eric Jervis et al.

Page 1 of 1

It is certified that error appears in the above-identified patent and that said Letters Patent is hereby corrected as shown below:

Column 31:
In claim 53, line 2, "said bathers" should read --said barriers--.

Column 32:
In claim 56, line 2, "said bathers" should read --said barriers--.

Column 32:
In claim 57, line 5, "said bathers" should read --said barriers--.

Column 32:
In claim 60, line 2, "said bathers" should read --said barriers--.

Signed and Sealed this
Thirteenth Day of September, 2011

David J. Kappos
*Director of the United States Patent and Trademark Office*

UNITED STATES PATENT AND TRADEMARK OFFICE
CERTIFICATE OF CORRECTION

PATENT NO. : 7,919,319 B2  
APPLICATION NO. : 10/582975  
DATED : April 5, 2011  
INVENTOR(S) : Eric Jervis et al.

Page 1 of 1

It is certified that error appears in the above-identified patent and that said Letters Patent is hereby corrected as shown below:

Column 31, line 62  
(claim 53, line 2) "said bathers" should read --said barriers--.

Column 32, line 2  
(claim 56, line 2) "said bathers" should read --said barriers--.

Column 32, line 5  
(claim 57, line 2) "said bathers" should read --said barriers--.

Column 32, line 12  
(claim 60, line 2) "said bathers" should read --said barriers--.

This certificate supersedes the Certificate of Correction issued September 13, 2011.

Signed and Sealed this  
Eleventh Day of October, 2011

David J. Kappos  
*Director of the United States Patent and Trademark Office*